(12) United States Patent
Bringhurst et al.

(10) Patent No.: US 7,479,478 B2
(45) Date of Patent: Jan. 20, 2009

(54) HUMAN PARATHYROID HORMONE MODIFICATIONS, PREPARATION AND USE

(75) Inventors: F. Richard Bringhurst, Walpole, MA (US); Hisashi Takasu, Mishima (JP); Thomas J. Gardella, Needham, MA (US); John T. Potts, Jr., West Newton, MA (US)

(73) Assignee: The General Hospital Corporation, Boston, MA (US)

( * ) Notice: Subject to any disclaimer, the term of this patent is extended or adjusted under 35 U.S.C. 154(b) by 479 days.

(21) Appl. No.: 10/959,605

(22) Filed: Oct. 7, 2004

(65) Prior Publication Data

US 2005/0203012 A1 Sep. 15, 2005

Related U.S. Application Data

(62) Division of application No. 10/157,076, filed on May 30, 2002, now Pat. No. 6,803,213, which is a division of application No. 09/448,867, filed on Nov. 24, 1999, now Pat. No. 6,417,333.

(60) Provisional application No. 60/109,938, filed on Nov. 25, 1998.

(51) Int. Cl.
*A61K 38/00* (2006.01)
*A61K 38/16* (2006.01)
*C07K 5/00* (2006.01)
*A61K 38/29* (2006.01)

(52) U.S. Cl. .................. 514/2; 514/12; 424/198.1; 530/300; 530/399

(58) Field of Classification Search .................. None
See application file for complete search history.

(56) References Cited

U.S. PATENT DOCUMENTS

| | | | |
|---|---|---|---|
| 5,350,836 A | 9/1994 | Kopchick et al. | |
| 5,556,940 A | 9/1996 | Willick et al. | |
| 6,417,333 B1 | 7/2002 | Bringhurst et al. | |
| 6,495,662 B1 | 12/2002 | Gardella et al. | |
| 6,537,965 B1 | 3/2003 | Bringhurst et al. | |
| 6,541,220 B1 | 4/2003 | Juppner et al. | |
| 6,803,213 B2 | 10/2004 | Bringhurst et al. | |
| 2003/0144209 A1 | 7/2003 | Bringhurst et al. | |
| 2003/0162256 A1 | 8/2003 | Juppner et al. | |
| 2003/0166838 A1 | 9/2003 | Gardella et al. | |
| 2005/0026839 A1 | 2/2005 | Gardella et al. | |

FOREIGN PATENT DOCUMENTS

| | | |
|---|---|---|
| CA | 2126299 | 12/1995 |
| EP | 0 748 817 | 12/1996 |
| GB | 2 269 176 | 2/1994 |
| WO | WO 91/05050 | 4/1991 |
| WO | WO 98/05683 | 12/1998 |
| WO | WO 99/18945 | 4/1999 |
| WO | WO 00/23594 | 4/2000 |
| WO | WO 00/31266 | 6/2000 |
| WO | WO 00/39278 | 7/2000 |
| WO | WO 00/40698 | 7/2000 |
| WO | WO 01/23427 | 4/2001 |
| WO | WO 03/009804 | 2/2003 |
| WO | WO 2004/067021 | 8/2004 |
| WO | WO 2004/093902 | 11/2004 |
| WO | WO 2005/009358 | 2/2005 |

OTHER PUBLICATIONS

Pettit and Gombotz, 1998, TIBTECH, 16: 343-349.*
Matsumoto, et al, 2006, Osteoporos. Int., 17: 1532-1538.*
Abou-Samra, A-B., et al., "Expression cloning of a common receptor for parathyroid hormone and parathyroid hormone-related peptide from rat osteoblast-like cells: A single receptor stimulates intracellular accumulation of both cAMP and inositol triphosphates and increases intracellular free calcium," *Proc. Natl. Acad. Sci. USA* 89:2732-2736, National Academy of Sciences (1992).
Azarani, A., et al., "Structurally Diverse N-terminal Peptides of Parathyroid Hormone (PTH) and PTH-related Peptide (PTHRP) Inhibit the Na+/H+ Exchanger NHE3 Isoform by Binding to the PTH/PTHRP Receptor Type I and Activating Distinct Signaling Pathways," *J. Biol. Chem.* 271:14931-14936, The American Society for Biochemistry and Molecular Biology, Inc. (1996).
Brenner, S.E., "Errors in genome annotation," *Trends Genet.* 15:132-133, Elsevier Science (1999).
Bringhurst, F.R., et al., "Cloned, Stably Expressed Parathyroid Hormone (PTH)/PTH-Related Peptide Receptors Activate Multiple Messenger Signals and Biological Responses in LLC-PK1 Kidney Cells," *Endocrinol.* 132:2090-2098, The Endocrine Society (1993).
Chakravarthy, B.R., et al., "Parathyroid Hormone Fragment [3-34] Stimulates Protein Kinase C (PKC) Activity in Rat Osteosarcoma and Murine T-Lymphoma Cells," *Biochem. Biophys. Res. Comm.* 171:1105-1110, Academic Press, Inc. (1990).
Chu, L.L.H., et al., "Porcine Proparathyroid Hormone. Identification, Biosynthesis, and Partial Amino Acid Sequence," *Biochem.* 14:3631-3635, American Chemical Society (1975).
Civitelli, R., et al., "PTH elevates inositol polyphosphates and diacylglycerol in a rat osteoblast-like cell line," *Am. J. Physiol.* 255:E660-E667, American Physiological Society (1988).
Cole, J.A., et al., "Regulation of Sodium-Dependent Phosphate Transport by Parathyroid Hormone in Opossum Kidney Cells: Adenosine 3', 5'-Monophosphate-Dependent and -Independent Mechanisms," *Endocrinol.* 122:2981-2989, The Endocrine Society (1988).
Donahue, H.J., et al., "Differential Effects of Parathyroid Hormone and Its Analogues on Cytosolic Calcium Ion and cAMP Levels in Cultured Rat Osteoblast-like Cells," *J. Biol. Chem.* 263:13522-13527, The American Society for Biochemistry and Molecular Biology, Inc. (1988).

(Continued)

*Primary Examiner*—Elizabeth C Kemmerer
*Assistant Examiner*—Sandra Wegert
(74) *Attorney, Agent, or Firm*—Clark & Elbing LLP

(57) ABSTRACT

The present invention is related to synthetic and/or recombinant biologically active peptide derivatives of PTH(1-28). Some of the peptides of the invention are at least 90% identical to a peptide consisting essentially of the amino acid sequence $X_{01}$ValSerGluIleGlnLeuMetHis AsnLeuGlyLys HisLeuAsnSer Met$X_{02}$ArgValGluTrpLeuArgLysLysLeu (SEQ ID NO:1), wherein $X_{01}$ is Ser, Ala or Gly; and $X_{02}$ is Glu or Arg.

15 Claims, 4 Drawing Sheets

OTHER PUBLICATIONS

Dunlay, R., and Hruska, K., "PTH receptor coupling to phospholipase C is an alternate pathway of signal transduction in bone and kidney," *Am. J. Physiol.* 258:F223-F231, American Physiological Society (1990).

Fujimori, A., et al., "Dissociation of Second Messenger Activation by Parathyroid Hormone Fragments in Osteosarcoma Cells," *Endocrinol.* 128:3032-3039, The Endocrine Society (1991).

Fujimori, A., et al., "Structure-Function Relationship of Parathyroid Hormone: Activation of Phospholipase-C, Protein Kinase-A and -C in Osteosarcoma Cells," *Endocrinol.* 130:29-36, The Endocrine Society (1992).

Gardella, T.J., et al., "Parathyroid Hormone (PTH)-PTH-related Peptide Hybrid Peptides Reveal Functional Interactions between the 1-14 and 15-34 Domains of the Ligand," *J. Biol. Chem.* 270:6584-6588, The American Society for Biochemistry and Molecular Biology, Inc. (1995).

Gombert, F.O., et al., "Alanine and D-Amino Acid Scan of Human Parathyroid Hormone," in *Peptides: Chemistry, Structure and Biology. Proceedings of the 14th American Peptide Symposium*, Jun. 18-23, Kaumaya, P.T.P., and Hodges, R.S., eds., Mayflower Scientific Ltd., Kingswinford, UK, pp. 661-662 (1996).

Guo, J., et al., "Parathyroid Hormone (PTH)/PTH-Related Peptide Receptor Density Modulates Activation of Phospholipase C and Phosphate Transport by PTH in LLC-PK1 Cells," *Endocrinol.* 136:3884-3891, The Endocrine Society (1995).

Hilliker, S., et al., "Truncation of the Amino Terminus of PTH Alters Its Anabolic Activity on Bone In Vivo," *Bone* 19:469-477, Elsevier Science (1996).

Janulis, M., et al., "Structure-Function Requirements of Parathyroid Hormone for Stimulation of 1,25-Dihydroxyvitamin D3 Production by Rat Renal Proximal Tubules," *Endocrinol.* 133:713-719, The Endocrine Society (1993).

Jobert, A-S., et al., "Parathyroid Hormone-Induced Calcium Release from Intracellular Stores in a Human Kidney Cell Line in the Absence of Stimulation of Cyclic Adenosine 3',5'-Monophosphate Production," *Endocrinol.* 138:5282-5292, The Endocrine Society (1997).

Jouishomme, H., et al., "Further Definition of the Protein Kinase C Activation Domain of the Parathyroid Hormone," *J. Bone Min. Res.* 9:943-949, Mary Ann Liebert, Inc. (1994).

Jouishomme, H., et al., "The Protein Kinase-C Activation Domain of the Parathyroid Hormone," *Endocrinol.* 130:53-60, The Endocrine Society (1992).

Jüppner, H., et al., "A G Protein-Linked Receptor for Parathyroid Hormone and Parathyroid Hormone-Related Peptide," *Science* 254:1024-1026, American Association for the Advancement of Science (1991).

Kronenberg, H.M., et al., "The PTH/PTHrP Receptor: One Receptor for Two Ligands," in *Molecular Genetics of Endocrine Disorders*, Thakker, R.V., ed., Chapman & Hall Medical, London, England, pp. 389-420 (1977).

Neugebauer, W., et al., "Solution Structure and Adenylyl Cyclase Stimulating Activities of C-Terminal Truncated Human Parathyroid Hormone Analogues," *Biochem.* 34:8835-8842, American Chemical Society (1995).

Pines, M., et al., "Inositol 1-,4-,5-Trisphosphate-Dependent Ca2+ Signaling by the Recombinant Human PTH/PTHrP Receptor Stably Expressed in a Human Kidney Cell Line," *Bone* 18:381-389, Elsevier (1996).

Reid, I.R., et al., "Parathyroid hormone acutely elevates intracellular calcium in osteoblastlike cells," *Am. J. Physiol.* 253:E45-E51, American Physiological Society (1987).

Rixon, R.H., et al., "Parathyroid Hormone Fragments May Stimulate Bone Growth in Ovariectomized Rats by Activating Adenylyl Cyclase," *J. Bone Min. Res.* 9:1179-1189, Mary Ann Liebert, Inc. (1994).

Schneider, H., et al., "A C-terminally truncated human parathyroid hormone receptor is functional and activates multiple G proteins," *FEBS Letts.* 351:281-285, Elsevier Science (1994).

Schneider, H., et al., "Cloning and functional expression of a human parathyroid hormone receptor," *Eur. J. Pharamcol.* 246:149-155, Elsevier Science B.V. (1993).

Segre, G.V., et al., "Characterization of Parathyroid Hormone Receptors in Canine Renal Cortical Plasma Membranes Using a Radioiodinated Sulfur-free Hormone Analogue," *J. Biol. Chem.* 254:6980-6986, The American Society of Biological Chemists Inc. (1979).

Seuwen, K., and Boddeke, H.G.W.M., "Heparin-insensitive calcium release from intracellular stores triggered by the recombinant human parathyroid hormone receptor," *Br. J. Pharmacol.* 114:1613-1620, Stockton Press (1995).

Siegfried, G., et al., "Parathyroid Hormone Stimulates Ecto-5'-Nucleotidase Activity in Renal Epithelial Cells: Role of Protein Kinase-C," *Endocrinol.* 136:1267-1275, The Endocrine Society (1995).

Smith, T.F., and Zhang, X., "The challenges of genome sequence annotation or 'The devil is in the details'," *Nat. Biotech.* 15:1222-1223, Nature America Inc. (1997).

Takasu, H., and Bringhurst, P.R., "Type-1 Parathyroid Hormone (PTH)/PTH-Related Peptide (PTHrP) Receptors Activate Phospholipase C in Response to Carboxyl-Truncated Analogs of PTH(1-34)," *Endocrinol.* 139:4293-4299, The Endocrine Society (1998).

Takasu, H., et al., "Amino-Terminal Modifications of Human Parathyroid Hormone (PTH) Selectively Alter Phospholipase C Signaling via the Type 1 PTH Receptor: Implications for Design of Signal-Specific PTH Ligands," *Biochem.* 38:13453-13460, American Chemical Society (1999).

Takasu, H., et al., "Dual Signaling and Ligand Selectivity of the Human PTH/PTHrP Receptor," *J. Bone Min. Res.* 14:11-20, Blackwell Science, Inc. (1999).

Takasu, H., et al., "Human PTH/PTHrP Receptors and Type-2 PTH Receptors Show Discordant Selectivity for Human PTH Analogs with Amino-Terminal Modifications," *Bone* 23:S255, Abstract T223, Elsevier Science (1998).

Takasu, H., et al., "Phospholipase C Activation via the Human PTH/PTHrP Receptor Requires an Intact Amino-Terminus of the Human PTH," *Bone* 23:S447, Abstract F148, Elsevier Science (1998).

Tamura, T., et al., "Parathyroid Hormone 1-34, But Not 3-34 or 7-34, Transiently Translocates Protein Kinase C in Cultured Renal (OK) Cells," *Biochem. Biophys. Res. Comm.* 159:1352-1358, Academic Press, Inc. (1989).

Tregear, G.W., and Potts, Jr., J.T., "Synthetic Analogues of Residues 1-34 of Human Parathyroid Hormone: Influence of Residue No. 1 on Biological Potency In Vitro," *Endocrine Res. Comm.* 2:561-570, Marcel Dekker, Inc. (1975).

Tregear, G.W., et al., "Bovine Parathyroid Hormone: Minimum Chain Length of Synthetic Peptide Required for Biological Activity," *Endocrinol.* 93:1349-1353, J.B. Lippincott Co. (1973).

Wells, J.A., "Additivity of Mutational Effects in Proteins," *Biochem.* 29:8509-8517, American Chemical Society (1990).

Whitfield, J.F., and Morley, P., "Small bone-building fragments of parathyroid hormone: new therapeutic agents for osteoporosis," *Trends Pharmacol. Sci.* 16:382-386, Elsevier Science (1995).

International Search Report for International Application No. PCT/US99/27863, mailed Mar. 3, 2000, European Patent Office, Rijswijk, Netherlands.

U.S. Appl. No. 09/475,158, Gardella et al., filed Dec. 30, 1999 (Not Published).

U.S. Appl. No. 09/672,020, Gardella et al., filed Sep. 29, 2000 (Not Published).

U.S. Appl. No. 09/869,565, Gardella et al., filed Oct. 17, 2001, U.S. National Phase of PCT Patent Publication No. WO 00/40698, Document AO2.

* cited by examiner

HUMAN PARATHYROID HORMONE MODIFICATIONS, PREPARATION AND USE

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

This work was supported by National Institutes of Health Grant DK 1 1794.

This application claims the benefit of the filing date of provisional application 60/109,938 filed on Nov. 25, 1998, which is herein incorporated by reference.

BACKGROUND OF THE INVENTION

1. Field of the Invention

The present invention relates to novel parathyroid hormone peptide (PTH) derivatives. In particular, the invention relates to PTH derivatives having one or more amino acid substitutions that confer PTH-1 receptor agonist or antagonist properties to the derivatives.

2. Description of Related Art

Full understanding of the complex biological roles of parathyroid hormone (PTH) and efforts to utilize its therapeutic potential require dissection of the multiple signaling patterns and cellular pathways of action of the hormone. PTH binds and activates specific receptors in renal and osseous target cells that also recognize PTH-related peptide (PTHrP) (Kronenberg, H., et al., "The PTH/PTHrP receptor: one receptor for two ligands," in *Genetics of Endocrine and Metabolic Disorders*, Thakker, R., ed., Chapman & Hall, London (1997), pp. 389-420). In renal and osteoblastic cell lines, PTH triggers several parallel intracellular signaling responses, including activation of adenylyl cyclase (AC), protein kinase A (PKA), phospholipase C (PLC) and protein kinase C (PKC) and generation of second messengers such as cyclic AMP (cAMP), inositol trisphosphate (IP$_3$), diacylglycerol and increased cytosolic free calcium (Ca$_i^{++}$) (Abou-Samra, A. B., et al., *Proc. Natl. Acad. Sci. USA.* 89(7):2732-2736 (1992); Azarani, A., et al., *J. Biol. Chem.* 271(25): 14931-14936 (1996); Bringhurst, F. R., et al., *Endocrinology* 132(5):2090-2098 (1993); Civitelli, R., et al., *Am. J. Physiol.* 255(5 Pt 1):E660-667 (1988); Donahue, H. J., et al., *J. Biol. Chem.* 263:13522-13527 (1988); Dunlay, R., and Hruska, K., *Am. J. Physiol.* 258(2 Pt 2):F223-231 (1990); Fujimori, A., et al., *Endocrinology* 128(6):3032-3039 (1991); Fujimori, A., et al., *Endocrinology* 130(1):29-36 (1992); Guo, J., et al., *Endocrinology* 136(9):3884-3891 (1995); Janulis, M., et al, *Endocrinology* 133:713-719 (1993); Jouishomme, H., et al., *J. Bone Miner. Res.* 9(6):943-949 (1994); Juppner, H., et al., *Science* 254(5034):1024-1026 (1991); Pines, M., et al., *Bone* 18(4): 381-389 (1996); Seuwen, K., et al., *Brit. J. Pharm.* 114(8): 1613-1620 (1995); Siegfried, G., et al., *Endocrinology* 136 (3):1267-1275 (1995).

To date, two structurally related but distinct species of PTH receptors have been cloned (Abou-Sarnra, A. B., et al., *Proc. Natl. Acad. Sci. U.S.A.* 89(7):2732-2736 (1992); Usdin, T. B., et al., *J. Biol. Chem.* 270(26):15455-15458 (1995); Schipani, E., et al., *Endocrinology*-132(5):2157-2165 (1993)). The first of these, type A, was isolated from both bone and kidney cells and shown to transduce multiple signaling responses to PTH-(1-34) or PTHrP(1-36) when heterologously expressed in cells that lack endogenous type 1 PTH/PTHrP receptors (hereinafter PTH-1 receptors) (Abou-Samra, A. B., et al., *Proc. Natl. Acad. Sci. U.S.A.* 89(7):2732-2736 (1992); Azarani, A., et al., *J. Biol. Chem.* 271(25):14931-14936 (1996); Bringhurst, F. R., et al., *Endocrinology* 132(5):2090-2098 (1993); Guo, J., et al., *Endocrinology* 136(9):3884-3891 (1995); Pines, M., et al., *Bone* 18(4):381-389 (1996); Jobert, A.-S., et al., *Endocrinology* 138(12):5282-5292 (1997); Schneider, H., et al., *Eur. J. Pharm.* 246(2):149-155 (1993)).

Previous efforts to define the contributions of specific regions of the PTH molecule to its binding and signaling properties have been undertaken mainly by use of complex in vivo bioassays, organ cultures, isolated cell membranes or cell lines, generally of rodent origin, that may express more than one type of endogenous PTH-1 receptors (Janulis, M., et al., *Endocrinology* 133:713-719 (1993); Siegfried, G., et al., *Endocrinology* 136(3):1267-1275 (1995); Yamamoto, S., et al., *Endocrinology* 138:2066-2072 (1997); Jouishomme, H., et al., *Endocrinology* 130(1):53-60 (1992); Segre, G. V., et al., *J. Biol. Chem.* 254:6980-6986 (1979); Tregear, G. W., and Potts, J. T., Jr. *Endocr. Res. Commun.* 2:561-567 (1975); Takasu, H., et al., *Endocrinology* 137(12):5537-5543 (1996); Orloff, J. J., et al., *Am. J. Physiol.* 262(5 Pt 1):E599-607 (1992)).

Early structure/function studies of bovine PTH-(1-34), performed with isolated renal membranes, identified the key role of the carboxyl(C)-terminal bPTH-(25-34) region for receptor binding and of the amino(N)-terminus (i.e., Ser[1]) for AC activation (Segre, G. V., et al., *J. Biol. Chem.* 254:6980-6986 (1979); Tregear, G. W., and Potts, J. T., Jr. *Endocr. Res. Commun.* 2:561-567 (1975)). Later work conducted in vitro with intact renal tubules or with cultured renal or bone cells, however, indicated that N-truncated analogs such as PTH-(3-34), although unable to stimulate AC, could fully activate PKC and could regulate certain PKC-dependent distal biologic responses (Janulis, M., et al., *Endocrinology* 133:713-719 (1993); Siegfried, G., et al., *Endocrinology* 136(3):1267-1275 (1995); Jouishomme, H., et al., *Endocrinology* 130(1): 53-60 (1992)). Amino-truncated analogs of PTH-(1-34) also were found to increase PLC activity or Ca$_i^{++}$ in some cells (Donahue, H. J., et al., *J. Biol. Chem.* 263:13522-13527 (1988); Fujimori, A., et al., *Endocrinology* 128(6):3032-3039 (1991); Siegfried, G., et al., *Endocrinology* 136(3):1267-1275 (1995)) though not in others (Reid, I. R., et al., *Am. J. Physiol.* 253(1 Pt 1):E45-51 (1987); Tamura, T., et al., *Biochem. Biophys.,Res. Commun.* 159:1352-1358 (1989)). Studies of the signaling properties of the cloned PTH-1 receptor have focused almost exclusively upon activation of AC, PLC or Ca$_i^{++}$ (Abou-Samra, A. B., et al., *Proc. Natl. Acad. Sci. U.S.A.* 89(7):2732-2736 (1992); Bringhurst, F. R., et al., *Endocrinology* 132(5):2090-2098 (1993); Guo, J., et al., *Endocrinology* 136(9):3884-3891 (1995); Pines, M., et al., *Bone* 18(4):381-389 (1996); Jobert, A.-S., et al., *Endocrinology* 138(12):5282-5292 (1997); Schneider, H., et al., *Eur. J. Pharm.* 246(2):149-155 (1993)), although stimulation of PKC and of PKC-dependent ion transport by hPTH(1-34), hPTH-(3-34) and other hPTH fragments was reported in CHO cells transfected with rat PTH-1 receptor cDNA (Azarani, A., et al., *J. Biol. Chem.* 271(25):14931-14936 (1996)).

Collectively, these observations have engendered the concept that the structural determinants for activation of AC/PKA signaling are distinct from those required for activation of PLC or PKC and that these reside, respectively, within the N- and C-terminal domains of PTH-(1-34) (Jouishomme, H., et al, *J. Bone Miner. Res.* 9(6):943-949 (1994); Tregear, G. W., and Potts, J. T., Jr. *Endocr. Res. Commun.* 2:561-567 (1975); Whitfield, J. F., and Morley, P. *Trends Pharm. Sci.* 16(11): 382-386 (1995)). In particular, the region hPTH-(29-32) was identified specifically as a critical PKC activation domain (Jouishomme, H., et al., *J. Bone Miner. Res.* 9(6):943-949 (1994); Whitfield, J. F., and Morley, P. *Trends Pharm. Sci.* 16(11):382-386 (1995)).

Compared with what is known from these studies of the rat PTH-1 receptor, much less information is available regarding the structural features of human PTH required for binding to the human PTH-1 receptor or for activation of its various signaling modes. Alanine-scanning mutagenesis has highlighted the importance of the C-terminal portion of hPTH-(1-34) for binding to the rat PTH-1 receptor (30). Functional studies of transfected human PTH receptors in COS-7 or HEK 293 cells have confirmed that hPTH-(1-34) activates AC and $Ca_i^{++}$, although stimulation of PLC was not observed consistently and responses that were reported were modest (Pines, M., et al., *Bone* 18(4):381-389 (1996); Seuwen, K., et al., *Brit. J. Pharm.* 114(8):1613-1620(1995); Jobert, A.-S., et al., *Endocrinology* 138(12):5282-5292 (1997); Schneider, H., et al., *FEBS Lett.* 351(2):281-285 (1994); ). The effects of hPTH-(3-34) on $Ca_i^{++}$ are similarly controversial (Pines, M., et al., *Bone* 18(4):381-389 (1996); Jobert, A.-S., et al., *Endocrinology* 138(12):5282-5292 (1997)), while the roles of other regions of the hPTH-(1-34) molecule in signaling via the human PTH-1 receptor have not been systematically addressed. Synthetic hPTH-(1-30)$NH_2$, hPTH-(1-29)$NH_2$, hPTH-(1-28)$NH_2$, hPTH-(1-27)$NH_2$, and hPTH-(1-26)$NH_2$ were each incapable of stimulating the activity of membrane-bound PKCs in osteoblast-like ROS 17/2 cells (Neugebauer et al. (*Biochem* 34: 8835-8842 (1995)).

SUMMARY OF THE INVENTION

The relatively large size of native PTH presents challenges to the use of these peptides as treatments for osteoporosis. In general, a protein of this size is not suitable for use as a drug, since it cannot be delivered effectively by simple methods such as nasal inhalation. Instead, injection is required, and in the case of PTH, daily, or almost daily injections would most likely be needed to achieve increases in bone formation rates. Additionally, larger peptides are technically difficult and expensive to prepare by conventional synthetic chemistry methods. Alternative methods employing recombinant DNA and cell-based expression systems are also expensive, potentially vulnerable to contamination by foreign proteins and do not circumvent the delivery problem.

Accordingly, it would be advantageous for those skilled in the art to be able to identify a small molecule analog (either peptide or non-peptide) that is based on the larger peptide and yet which still retains the desired biological activities. The activity may at first be weak relative to the intact peptide, but further optimization can lead to enhanced efficacy and potency.

The inventors recently observed that hPTH-(1-31), shown by others to be a full AC agonist but to be incapable of activating PKC via rodent PTH-1 receptors (Jouishomme, H., et al., *Endocrinology* 130(1):53-60 (1992)), was as potent as hPTH-(1-34) in activating both AC and PLC via human PTH-1 receptors expressed in LLC-PK1, COS-7 or HEK 293 cells (Takasu, H., and Bringhurst, F. R., *Endocrinology* 139 (10): 4293-4299(1998)). These unexpected observations prompted us to undertake a more detailed analysis of the relative roles of the N- and C-terminal regions of hPTH-(1-34) in binding to, and activation of, the human PTH-1 receptor, with a particular focus on PLC activation. The present invention is directed to amino/carboxy terminal modifications of human parathyroid hormone which selectively alter phospholipase C signaling via the PTH-1 receptor. This unexpected finding has important implications for the design of signal specific PTH ligands. Such signal-specific ligands will be useful in triggering only a desired subset of PTH actions and therefore signal-specific ligands may have unique advantages not matched by the complete set of PTH actions.

The present invention relates to PTH(1-28) peptides and derivatives thereof. Compounds of the invention which include PTH(1-28) peptides, fragments thereof, derivatives thereof, pharmaceutically acceptable salts thereof, and N- or C-derivatives thereof, are hereinafter collectively referred to as "compounds of SEQ ID NO: 1 and derivatives thereof."

The invention provides synthetic and/or recombinant biologically active peptide derivatives of PTH(1-28). In one specific embodiment, the invention provides a biologically active peptide at least 90% identical to a peptide consisting essentially of the formula:
 (a) $X_{01}$ValSerGluIleGlnLeuMetHisAsnLeuGly LysHisLeuAsnSerMet$X_{02}$ArgValGluTrpLeuArgLys LysLeu (SEQ ID NO:1);
 (b) fragments thereof containing amino acids 1-24, 1-25, 1-26, or 1-27;
 (c) pharmaceutically acceptable salts thereof; or
 (d) N- or C-derivatives thereof;
 wherein:
  $X_{01}$ is Ser, Ala or Gly; and
  $X_{02}$ is Glu or Arg,
provided that said peptide is not hPTH(1-26)$NH_2$, hPTH(1-27)$NH_2$ or hPTH(1-28)$NH_2$.

In accordance with yet a further aspect, this invention also provides pharmaceutical compositions comprising
 (a) a biologically active peptide at least 90% identical to a peptide consisting essentially of the formula:
$X_{01}$ValSerGluIleGlnLeuMetHisAsnLeuGlyLysAsnSerMet $X_{02}$ArgValGlu TrpLeuArgLysLysLeu (SEQ ID NO:1);
 (b) fragments thereof containing amino acids 1-24, 1-25, 1-26, or 1-27;
 (c) pharmaceutically acceptable salts thereof; or
 (d) N- or C-derivatives thereof;
 wherein:
  $X_{01}$ is Ser, Ala or Gly; and
  $X_{02}$ is Glu or Arg; and a pharmaceutically acceptable carrier.

In accordance with yet a further aspect, this invention provides a nucleic acid molecule consisting essentially of a polynucleotide encoding a biologically active peptide which has an amino acid sequence selected from the group consisting of:
 (a) $X_{01}$ValSerGluIleGlnLeuMetHisAsnLeuGlyLysHis LeuAsnSerMet$X_{02}$ArgValGluTrpLeuArgLysLysLeu (SEQ ID NO:1);
 (b) fragments thereof containing amino acids 1-24, 1-25, 1-26, or 1-27;
 wherein:
  $X_{01}$ is Ser, Ala or Gly; and
  $X_{02}$ is Glu or Arg.

In accordance with yet a further aspect, this invention provides a recombinant DNA molecule comprising: (1) an expression control region, said region in operable linkage with (2) a polynucleotide sequence coding for a biologically active peptide, wherein said peptide is selected from the group consisting of:
 (a) $X_{01}$ValSerGluIleGlnLeuMetHisAsnLeuGlyLys His LeuAsnSerMet$X_{02}$ArgValGluTrpLeuArgLysLysLeu (SEQ ID NO:1);
 (b) fragments thereof containing amino acids 1-24, 1-25, 1-26, or 1-27;

wherein:
    $X_{01}$ is Ser, Ala or Gly; and
    $X_{02}$ is Glu or Arg.

In accordance with yet a further aspect, this invention provides a method for treating mammalian conditions characterized by decreases in bone mass, which method comprises administering to a subject in need thereof an effective bone mass-increasing amount of a biologically active peptide, wherein said peptide comprises an amino acid sequence at least 90% identical to a member selected from the group consisting essentially of:

(a) $X_{01}$ValSerGluIleGlnLeuMetHisAsnLeuGlyLysHisLeuAsnSerMet$X_{02}$ArgValGluTrpLeuArgLysLysLeu (SEQ ID NO:1);

(b) fragments thereof containing amino acids 1-24, 1-25, 1-26, or 1-27;

(c) pharmaceutically acceptable salts thereof; or (d) N- or C-derivatives thereof;

wherein:
    $X_{01}$ is Ser, Ala or Gly; and
    $X_{02}$ is Glu or Arg, provided that said peptide is not hPTH(1-26)$NH_2$, hPTH(1-27)$NH_2$ or hPTH(1-28)$NH_2$; and a pharmaceutically acceptable carrier.

In accordance with yet a further aspect, there is provided a method for treating a medical disorder that results from altered or excessive action of the PTH-1/PTH-2 receptor, comprising administering to a patient a therapeutically effective amount of a biologically active peptide wherein said peptide comprises an amino acid sequence at least 90% identical to a member selected from the group consisting essentially of:

(a)$X_{01}$ValSerGluIleGlnLeuMetHisAsnLeuGlyLysHisLeuAsnSerMet$X_{02}$ArgValGluTrpLeuArgLysLysLeu (SEQ ID NO:1);

(b) fragments thereof containing amino acids 1-24, 1-25, 1-26, or 1-27;

(c) pharmaceutically acceptable salts thereof; or (d) N- or C-derivatives thereof;

wherein:
    $X_{01}$ is Ser, Ala or Gly; and
    $X_{02}$ is Glu or Arg, provided that said peptide is not hPTH(1-26)$NH_2$, hPTH(1-27)$NH_2$ or hPTH(1-28)$NH_2$; and a pharmaceutically acceptable carrier sufficient to inhibit activation of the PTH-1/PTH-2 receptor of said patient In accordance with yet a further aspect, this invention also provides a method for determining rates of bone formation, bone resorption and/or bone remodeling comprising administering to a patient an effective amount of a labeled peptide of SEQ ID NO: 1 or a derivative thereof and determining the uptake of said peptide into the bone of said patient. The peptide may be labeled with a label selected from the group consisting of: radiolabel, flourescent label, bioluminescent label, or chemiluminescent label. An example of a suitable radiolabel is $^{99m}Tc$.

In accordance with yet a further aspect of the invention, any amino-acid substitutions at positions 1-28, and more particularly those amino acid substitutions at amino acid positions 1 and/or 19, which do not destroy the biological activity of the PTH(1-28) peptide analog to agonize the PTH-1/PTH-2 receptor (as determined by assays known to the skilled artisan and discussed below), are also included within the scope of the present invention.

DETAILED DESCRIPTION OF THE PREFERRED EMBODIMENTS

Definitions

Figure 1:
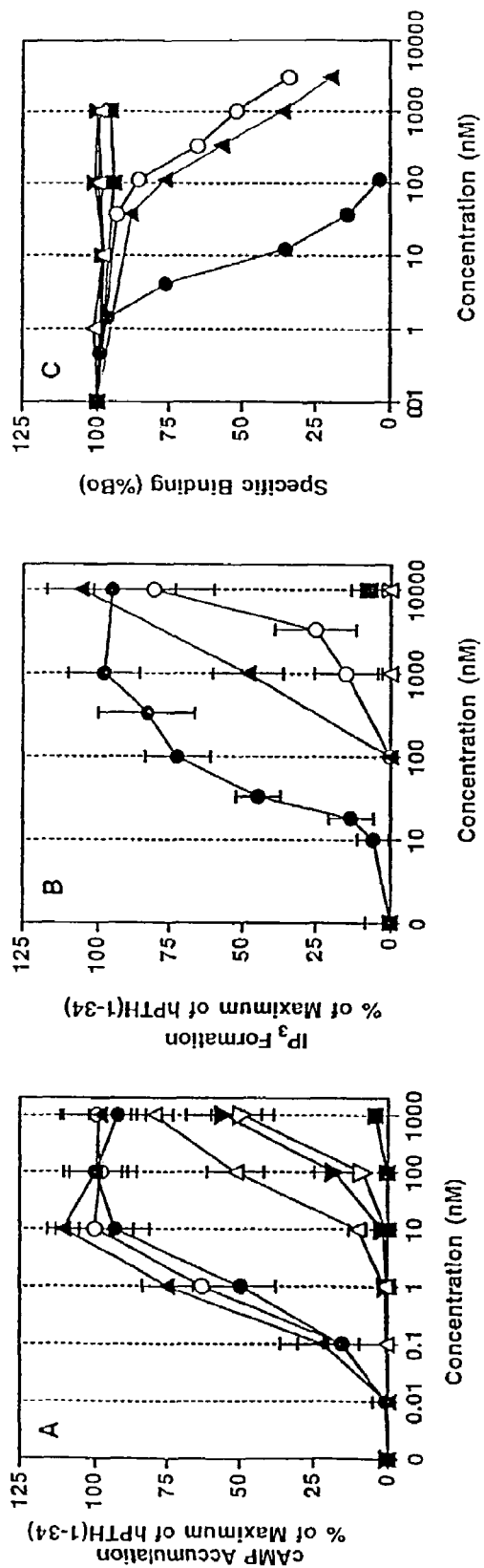
FIG. 1. Properties of C-terminally truncated hPTH analogs in HKRB B7 cells. Intracellular cAMP accumulation (A), IP3 formation (B) and competitive radioligand binding (C) are depicted for the indicated concentrations of: hPTH-(1-34) (●) (SEQ ID NO: 14), hPTH-(1-29) (▲) (SEQ ID NO: 16), hPTH-(1-28) (○) (SEQ ID NO: 12), hPTH-(1-27) (Δ) (SEQ ID NO: 13), hPTH-(1-26) (▼) (SEQ ID NO: 17), hPTH-(1-25) (∇) (SEQ ID NO: 18) and hPTH-(1-24) (■) (SEQ ID NO: 19). Results are expressed as percentages of the maximal responses to hPTH-(1-34) (A & B) (SEQ ID NO: 14) or the total specific binding of the $^{125}I$-$[Nle_{8,21}, Tyr_{34}]$rat PTH-(1-34) (SEQ ID NO: 23) radioligand (C) observed in the same assay. Each point represents the mean±SEM of results from several (i.e., 2-4) experiments, each of which was performed in triplicate (SEMs of binding data typically were less than 3% of total binding and thus often are obscured by the symbols).

In the description that follows, a number of terms used in recombinant DNA technology and peptide synthesis are utilized extensively. In order to provide a clear and consistent understanding of the specification and claims, including the scope to be given such terms, the following definitions are provided.

Cloning vector: A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector: A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Recombinant Host: According to the invention, a recombinant host may be any prokaryotic or eukaryotic host cell which contains the desired cloned genes on an expression vector or cloning vector. This term is also meant to include those prokaryotic or eukaryotic cells that have been genetically engineered to contain the desired gene(s) in the chromosome or genome of that organism. For examples of such hosts, see Sambrook et al., *Molecular Cloning: A Laboratory Manual*, Second Edition, Cold Spring Harbor Laboratory, Cold Spring Harbor, N.Y. (1989). Preferred recombinant hosts are eukaryotic cells transformed with the DNA construct of the invention. More specifically, mammalian cells are preferred.

Promoter: A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter. Examples of promoters include the CMV promoter (In Vitrogen, San Diego, Calif.), the SV40, MMTV, and hMTIIa promoters (U.S. Pat. No. 5,457,034), the HSV-1 4/5 promoter (U.S. Pat. No. 5,501,979), and the early intermediate HCMV promoter (WO92/17581). Also, tissue-specific enhancer elements may be employed. Additionally, such promoters may include tissue and cell-specific promoters of an organsim.

Polynucleotide: This term generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

Polypeptide: This term refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in the research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. See, for instance, *Proteins-Structure and Molecular Properties,* 2nd Ed., T. E. Creighton, W.H. Freeman and Company, New York, 1993 and Wold, F., Posttranslational Protein Modifications: Perspectives and Prospects, pgs. 1-12 in *Posttranslational Covalent Modification of Proteins,* B. C. Johnson, Ed., Academic Press, New York, 1983; Seifter et al., "Analysis for protein modifications and nonprotein cofactors", *Methods in Enzymol.* 182:626-646 (1990) and Rattan et al., "Protein Synthesis: Posttranslational Modifications and Aging", *Ann NY Acad Sci* 663:48-62 (1992).

Homologous/Nonhomologous: Two nucleic acid molecules are considered to be "homologous" if their nucleotide sequences share a similarity of greater than 40%, as determined by HASH-coding algorithms (Wilber, W. J. and Lipman, D. J., *Proc. Natl. Acad. Sci.* 80:726-730 (1983)). Two nucleic acid molecules are considered to be "nonhomologous" if their nucleotide sequences share a similarity of less than 40%.

Isolated: A term meaning altered "by the hand of man" from the natural state. If a composition or substance occurs in nature, the isolated form has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated for purposes of the present invention. Also intended as an "isolated polypeptide" or an "isolated polynucleotide" are polypeptides or polynucleotides that have been purified, partially or substantially, from a recombinant host cell or from a native source. For example, a recombinantly produced version of compounds of SEQ ID NO:1 and derivatives thereof can be substantially purified by the one-step method described in Smith and Johnson, *Gene* 67:31-40 (1988).

Identity: This term refers to a measure of the identity of nucleotide sequences or amino acid sequences. In general, the sequences are aligned so that the highest order match is obtained. "Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carilo, H. & Lipton, D., *SIAM J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM J Applied Math* 48:1073 (1988). Methods to determine identity and similarity are codified in computer programs. Preferred computer program methods to determine identity and similarity between two sequences include, but are not limited to, GCG program package (Devereux, J., et al., *Nucleic Acids Research* 12(i):387 (1984)), BLASTP, BLASTN, FASTA (Atschul, S. F., et al., *J Molec Biol* 215:403 (1990)).

Fragment: A "fragment" of a molecule such as a compound of SEQ ID NO: 1 or derivative thereof is meant to refer to any polypeptide subset of these molecules.

Functional Derivative: The term "derivatives" is intended to include "variants," the "derivatives," or "chemical derivatives" of the molecule. A "variant" of a molecule such as a compound of SEQ ID NO: 1 or derivative thereof is meant to refer to a molecule substantially similar to either the entire molecule, or a fragment thereof. An "analog" of a molecule such as a compound of SEQ ID NO: 1 or derivative thereof is meant to refer to a non-natural molecule substantially similar to either the SEQ ID NO: 1 molecules or fragments thereof.

A molecule is said to be "substantially similar" to another molecule if the sequence of amino acids in both molecules is substantially the same, and if both molecules possess a similar biological activity. Thus, provided that two molecules possess a similar activity, they are considered variants, derivatives, or analogs as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

Biological Activity of the Protein: This expression refers to the metabolic or physiologic function of compounds of SEQ ID NO: 1 or derivatives thereof including similar activities or improved activities or those activities with decreased undesirable side-effects. Also included are antigenic and immunogenic activities of said compounds of SEQ ID NO: 1 or derivatives thereof.

Gene Therapy: A means of therapy directed to altering the normal pattern of gene expression of an organism. Generally, a recombinant polynucleotide is introduced into cells or tissues of the organism to effect a change in gene expression.

Host Animal: Transgenic animals, all of whose germ and somatic cells contain the DNA construct of the invention. Such transgenic animals are in general vertebrates. Preferred host animals are mammals such as non-human primates, mice, sheep, pigs, cattle, goats, guinea pigs, rodents, e.g. rats, and the like. The term Host Animal also includes animals in all stages of development, including embryonic and fetal stages.

I. Compounds of SEQ ID NO: 1 and Derivatives Thereof—Structural and Functional Properties Parathyroid hormone (PTH) and PTH-related peptide (PTHrP) activate the PTH/PTHrP receptor to trigger parallel increases in adenylyl cyclase (AC) and phospholipase C (PLC). The amino (N)-terminal region of PTH-(1-34) is essential for AC activation. Ligand domains required for activation of PLC, PKC and other effectors have been less well defined, although some studies in rodent systems have identified a core region (PTH-(29-32)) involved in PKC activation. To determine the critical ligand domain(s) for PLC activation, a series of truncated hPTH-(1-34) analogs were assessed using LLC-PKI cells that stably express abundant transfected human or rat PTH/PTHrP receptors.

Phospholipase C signaling and ligand binding affinity were reduced by carboxyl(C)-terminal truncation of hPTH-(1-34) but were coordinately restored when a binding-enhancing substitution (Glu$^{19}$→Arg$^{19}$) was placed within hPTH-(1-28), the shortest hPTH peptide that could fully activate both AC and PLC. Phospholipase C, but not AC, activity was reduced by substituting Gly$^1$ for Ser$^1$ in hPTH-(1-34) and was eliminated by removing either residue 1 or the α-amino group alone. These changes did not alter binding affinity. These findings led to the design of an analog, [Gly$^1$,Arg$^{19}$]hPTH-(1-28), that was markedly signal-selective, with full AC but no PLC activity. Thus, the extreme N-terminus of hPTH constitutes part of the activation domain for coupling to PLC. The C-terminal region, especially hPTH-(28-31), contributes to PLC activation through effects upon binding: the region hPTH-(29-34) clearly is not required for full PLC activation. The N-terminal determinants of AC and PLC activation in hPTH-(1-34) overlap but are not identical, as subtle modifications in this region may dissociate activation of these two effectors. The [Gly$^1$,Arg$^{19}$]hPTH-(1-28) analog, in particular, is useful in dissociating AC- from PLC-dependent actions of PTH.

The present invention relates to hPTH(1-28) peptides and derivatives thereof. Compounds of the invention which include hPTH(1-28) peptides, fragments thereof, derivatives thereof, pharmaceutically acceptable salts thereof, and N- or C-derivatives thereof, are hereinafter collectively referred to as "compounds of SEQ ID NO:1 and derivatives thereof."

In detail, the invention provides synthetic and/or recombinant biologically active peptide derivatives of hPTH(1-28). In one specific embodiment, this invention provides a biologically active peptide at least 90% identical to a peptide consisting essentially of the formula:

(a) $X_{01}$ValSerGluIleGlnLeuMetHisAsnLeuGlyLysHis LeuAsnSerMet$X_{02}$ArgValGluTrpLeuArgLysLysLeu (SEQ ID NO:1);

(b) fragments thereof containing amino acids 1-24, 1-25, 1-26, or 1-27;

(c) pharmaceutically acceptable salts thereof; or (d) N- or C-derivatives thereof;

wherein:

$X_{01}$ is Ser, Ala or Gly; and $X_{02}$ is Glu or Arg, provided that said peptide is not hPTH(1-26)NH$_2$, hPTH(1-27)NH$_2$ or hPTH(1-28)NH$_2$.

The present invention thus provides a novel hPTH (1-28) derivative that is a potent small signal selective PTH-1/PTH-2 receptor agonist. In a preferred embodiment, the hPTH (1-28) derivative is altered at residues 1 and 19. Most preferably, the invention includes an hPTH (1-28) derivative having an amino acid substitution of alanine or glycine for serine at position 1 of hPTH (1-28), as well as arginine for glutamine at position 19 of hPTH (1-28).

In addition, any other amino-acid substitutions of a nature, which do not destroy the ability of the hPTH (1-28) derivative to agonize or antagonize the PTH-1/PTH-2 receptor (as determined by assays known to the skilled artisan and discussed below), are included in the scope of the present invention.

As protein products, compounds of SEQ ID NO: 1 or derivatives thereof of the present invention are amenable to production by the technique of solution- or solid-phase peptide synthesis. The solid phase peptide synthesis technique, in particular, has been successfully applied in the production of human PTH and can be used for the production of compounds of SEQ ID NO: 1 or derivatives thereof of the present invention (for guidance, see Kimura et al., supra, and see Fairwell et al., *Biochem.* 22:2691 (1983)). Success with producing human PTH on a relatively large scale has been reported by Goud et al., in *J. Bone Min. Res.* 6(8):781 (1991), incorporated herein by reference. The synthetic peptide synthesis approach generally entails the use of automated synthesizers and appropriate resin as solid phase, to which is attached the C-terminal amino acid of the desired compounds of SEQ ID NO: 1 or derivatives thereof. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and trifluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984). It will be appreciated that the peptide synthesis approach is required for production of SEQ ID NO: 1 and derivatives thereof variants which incorporate amino acids that are not genetically encoded.

In accordance with another aspect of the present invention, substituents may be attached to the free amine of the N-terminal amino acid of compounds of SEQ ID NO: 1 or derivatives thereof by standard methods known in the art. For example, alkyl groups, e.g., $C_{1-12}$ alkyl, may be attached using reductive alkylation. Hydroxyalkyl groups, e.g. $C_{1-12}$ hydroxyalkyl, may also be attached using reductive alkylation wherein the free hydroxy group is protected with a t-butyl ester. Acyl groups, e.g., $COE_1$, may be attached by coupling the free acid, e.g., $E_1COOH$, to the free amino of the N-terminal amino acid. Also contemplated within the scope of this invention are those compounds of SEQ ID NO: 1 and derivatives thereof that alter secondary or tertiary structure, or stability of compounds of SEQ ID NO: 1 or derivatives thereof which still retain biological activity. Such derivatives might be achieved through lactam cyclization, disulfide bonds, or other means known to a person of ordinary skill in the art.

Among the most preferred embodiments of the invention are those compounds which serve as signal selective agonists of the PTH-1/PTH-2 receptor. In particular, preferred embodiments are those compounds where $X_{01}$ is Gly; and $X_{02}$ is Arg. The amino acid sequence of this preferred embodiment is thus GlyValSerGluIleGlnLeuMetHisAsnLeuGlyLysHisLeuAsnSerMetArgArgValGlu TrpLeu ArgLysLysLeu (SEQ ID NO: 2) or derivatives thereof. [[Gly$^1$Arg$^{19}$]hPTH(1-28)].

Another set of the preferred embodiments are those compounds having a one amino acid deletion at the carboxy terminus of SEQ ID NO: 2 where $X_{01}$ is Gly; and $X_{02}$ is Arg. The amino acid sequence of this preferred embodiment is thus GlyValSerGluIleGlnLeuMetHisAsnLeuGlyLysHis LeuAsnSerMetArgArgVal GluTrpLeuArgLysLys (SEQ ID NO: 3) or derivatives thereof. [[Gly$^1$Arg$^{19}$]hPTH(1-27)].

Among the preferred embodiments of the invention are those compounds which serve as non-signal selective agonists of the PTH-1/PTH-2 receptor. In particular, preferred embodiments are those compounds where $X_{01}$ is Ala; and $X_{02}$ is Arg. The amino acid sequence of this preferred embodiment is thus AlaValSerGluIleGlnLeuMetHisAsn LeuGlyLys HisLeuAsnSerMetArg ArgValGluTrpLeu ArgLysLysLeu (SEQ ID NO: 4) or derivatives thereof. [[Ala$^1$Arg$^{19}$]hPTH(1-28)].

Another set of the preferred embodiments are those compounds having a one amino acid deletion at the carboxy terminus of SEQ ID NO: 4 where $X_{01}$ is Ala; and $X_{02}$ is Arg. The amino acid sequence of this preferred embodiment is thus AlaValSerGluIleGlnLeuMetHisAsnLeuGly LysHis LeuAsnSerMetArgArgVal GluTrpLeuArgLysLys (SEQ ID NO: 5) or derivatives thereof. [[Ala$^1$Arg$^{19}$]hPTH(1-27)].

Another set of preferred embodiments are those compounds where $X_{01}$ is Ser; and $X_{02}$ is Arg. The amino acid sequence of this preferred embodiment is thus SerValSerGluIleGlnLeuMetHisAsnLeuGlyLysHisLeuAsnSerMetArgArgVal GluTrpLeuArgLys LysLeu (SEQ ID NO: 6) or derivatives thereof. [[Arg$^{19}$]hPTH(1-28)].

Another set of the preferred embodiments are those compounds having a one amino acid deletion at the carboxy terminus of SEQ ID NO: 6 where $X_{01}$ is Ser; and $X_{02}$ is Arg. The amino acid sequence of this preferred embodiment is thus SerValSerGluIleGlnLeuMetHisAsnLeuGlyLysHis LeuAsnSerMetArgArgVal GluTrpLeuArgLysLys (SEQ ID NO: 7) or derivatives thereof. [[Arg$^{19}$]hPTH(1-27)].

Another set of preferred embodiments are those compounds where $X_{01}$ is Ala; and $X_{02}$ is Glu. The amino acid sequence of this preferred embodiment is thus AlaValSerGluIleGlnLeuMetHisAsnLeuGlyLysHisLeuAsn SerMetGluArgVal GluTrpLeuArgLys LysLeu (SEQ ID NO: 8) or derivatives thereof. [[Ala$^1$]hPTH(1-28)].

Another set of the preferred embodiments are those compounds having a one amino acid deletion at the carboxy terminus of SEQ ID NO: 8 where $X_{01}$, is Ala; and $X_{02}$ is Glu. The amino acid sequence of this preferred embodiment is thus AlaValSerGluIleGlnLeuMetHisAsnLeuGly LysHis LeuAsnSerMetGluArgVal GluTrpLeuArgLysLys (SEQ ID NO: 9) or derivatives thereof. [[Ala$^1$]hPTH(1-27)].

Another set of preferred embodiments are those compounds where $X_{01}$ is Gly; and $X_{02}$ is Glu. The amino acid sequence of this preferred embodiment is thus GlyValSerGluIleGlnLeuMetHisAsnLeuGlyLysHisLeu AsnSerMetGluArgVal GluTrpLeuArgLysLysLeu (SEQ ID NO: 10) or derivatives thereof. [[Gly$^1$]hPTH(1-28)].

Another set of the preferred embodiments are those compounds having a one amino acid deletion at the carboxy terminus of SEQ ID NO: 10 where $X_{01}$ is Gly; and $X_{02}$ is Glu. The amino acid sequence of this preferred embodiment is thus GlyValSerGluIleGlnLeuMetHis- AsnLeuGlyLysHisLeuAsnSerMetGluArgVal GluTrpLeu ArgLysLys (SEQ ID NO: 11) or derivatives thereof. [[Gly$^1$] hPTH(1-27)].

Another set of preferred embodiments are those pharmaceutical compositions where $X_{01}$ is Ser; and $X_{02}$ is Glu. The amino acid sequence of this preferred embodiment is thus SerValSerGluIleGlnLeuMetHisAsnLeuGlyLysHis LeuAsnSerMetGluArgValGluTrpLeuArgLysLysLeu (SEQ ID NO: 12) or derivatives thereof. [hPTH(1-28)].

Another set of preferred embodiments are those pharmaceutical compositions where $X_{01}$ is Ser; and $X_{02}$ is Glu. The amino acid sequence of this preferred embodiment is thus SerValSerGluIleGlnLeuMetHisAsnLeuGlyLysHis LeuAsnSerMetGluArgValGluTrpLeuArgLysLys (SEQ ID NO: 13) or derivatives thereof. [hPTH(1-27)].

III. Vectors, Host Cells, and Recombinant Expression

The present invention also relates to vectors that comprise a polynucleotide of the present invention, and host cells which are genetically engineered with vectors of the invention and the production of polypeptides of the invention by recombinant techniques. Cell-free translation systems can also be employed to produce such proteins using RNAs derived from the DNA constructs of present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, *Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., Molecular Cloning: A Laboratory Manual (supra).

RNA vectors may also be utilized for the expression of the nucleic acids encoding compounds of SEQ ID NO: 1 or derivatives thereof disclosed in this invention. These vectors are based on positive or negative strand RNA viruses that naturally replicate in a wide variety of eukaryotic cells (Bredenbeek, P. J. & Rice, C. M., *Virology* 3: 297-310, 1992). Unlike retroviruses, these viruses lack an intermediate DNA life-cycle phase, existing entirely in RNA form. For example, alpha viruses are used as expression vectors for foreign proteins because they can be utilized in a broad range of host cells and provide a high level of expression; examples of viruses of this type include the Sindbis virus and Semliki Forest virus (Schlesinger, S., TIBTECH 11:18-22, 1993; Frolov, I., et al., Proc. Natl. Acad. Sci. (USA) 93: 11371-11377,1996). As exemplified by Invitrogen's Sinbis expression system, the investigator may conveniently maintain the recombinant molecule in DNA form (pSinrep5 plasmid) in the laboratory, but propagation in RNA form is feasible as well. In the host cell used for expression, the vector containing the gene of interest exists completely in RNA form and may be continuously propagated in that state if desired.

For secretion of the translated protein into the lumen of the endoplasmic reticulum, into the periplasmic space or into the extracellular environment appropriate secretion signals may be incorporated into the desired polypeptide. These signals may be endogenous to the polypeptide or they may be heterologous signals.

The expression of a DNA sequence requires that the DNA sequence be "operably linked" to DNA sequences which contain transcriptional and translational regulatory information. An operable linkage is a linkage in which the control or regulatory DNA sequences and the DNA sequence sought to be expressed are connected in such a way as to permit gene expression. The precise nature of the "control regions" needed for gene expression may vary from organism to organism, but shall in general include a promoter region which, in prokaryotic cells, contains both the promoter (which directs the initiation of RNA transcription) as well as DNA sequences which, when transcribed into RNA, will signal the initiation of protein synthesis. Regulatory regions in eukaryotic cells will in general include a promoter region sufficient to direct the initiation of RNA synthesis.

Two DNA sequences are said to be operably linked if the nature of the linkage between the two DNA sequences does not (1) result in the introduction of a frameshift mutation, (2) interfere with the ability of the promoter region sequence to direct the transcription of the fusion protein-encoding sequence or (3) interfere with the ability of the fusion protein-encoding sequence to be transcribed by the promoter region sequence. Thus, a promoter region would be operably linked to a DNA sequence if the promoter were capable of transcribing that DNA sequence.

The joining of various DNA fragments, to produce the expression vectors of this invention is performed in accordance with conventional techniques, employing blunt-ended or staggered-ended termini for ligation, restriction enzyme digestion to provide appropriate termini, filling in of cohesive ends as appropriate, alkali and phosphatase treatment to avoid undesirable joining, and ligation with appropriate ligases. In the case of a fusion protein, the genetic construct encodes an inducible promoter which is operably linked to the 5' gene sequence of the fusion protein to allow efficient expression of the fusion protein.

To express compounds of SEQ ID NO: 1 or derivatives thereof in a prokaryotic cell (such as, for example, *E. coli, B. subtilis, Pseudomonas, Streptomyces*, etc.), it is necessary to operably link the SEQ ID NO: 1-encoding DNA sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pBR325, etc. Examples of inducible prokaryotic promoters include the major right and left promoters of bacteriophage λ, (PL and PR), the trp, recA. lacZ. lacI. and gal promoters of *E. coli*, the α-amylase (Ulmanen, I. et al., *J. Bacteriol.* 162:176-182 (1985)), and the σ-28-specific promoters of *B. subtilis* (Gilman, M. Z. et al., *Gene* 32:11-20 (1984)), the promoters of the bacteriophages of *Bacillius* (Gryczan, T. J., In: *The Molecular Biology of the Bacilli*, Academic Press, Inc., NY (1982)), and *Streptomyces* promoters (Ward, J. M. et al., *Mol. Gen. Genet.* 203:468-478 (1986)). Prokaryotic promoters are reviewed by Glick, B. R., *J. Ind. Microbiol.* 1:277-282 (1987); Cenatiempo, Y., *Biochimie* 68:505-516 (1986)); and Gottesman, S., *Ann. Rev. Genet.* 18:415-442 (1984)).

If expression is desired in a eukaryotic cell, such as yeast, fungi, mammalian cells, or plant cells, then it is necessary to employ a promoter capable of directing transcription in such a eukaryotic host. Preferred eukaryotic promoters include the promoter of the mouse metallothionein I gene (Hamer, D. et al., *J. Mol. Appl. Gen.* 1:273-288 (1982)); the TK promoter of Herpes virus (McKnight, S., *Cell* 31:355-365 (1982)); the SV40 early promoter (Benoist, C., et al., *Nature (London)* 290:304-310 (1981)); and the yeast gal4 gene promoter (Johnston, S. A., et al., *Proc. Natl. Acad. Sci.* (*USA*) 79:6971-6975 (1982); Silver, P. A., et al., *Proc. Natl. Acad. Sci.* (*USA*) 81:5951-5955 (1984)).

Preferably, the introduced DNA sequence will be incorporated into a plasmid or viral vector capable of autonomous replication in the recipient host. Any of a wide variety of vectors may employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include, without limitation, plasmids such as those capable of replication in *E. coli* (such as, for example, pBR322, ColEl, pSC101, pACYC 184, πVX. Such plasmids are, for example, disclosed by Maniatis, T., et al., In: *Molecular Cloning*, A Laboratory Manual, Cold Spring Harbor Press, Cold Spring Harbor, N.Y. (1982)). Preferred plasmid expression vectors include the pGFP-1 plasmid described in Gardella et al., *J. Biol. Chem.* 265:15854-15859 (1989), or a modified plasmid based upon one of the pET vectors described by Studier and Dunn, *Methods in Enzymology* 185: 60-89 (1990). *Bacillus* plasmids include pC194, pC221, pT 127, etc. Such plasmids are disclosed by Gryczan, T. In: The Molecular Biology of the Bacilli, Academic Press, NY pp. 307-329 (1982). Suitable *Streptomyces* plasmids include pIJIOI (Kendall, K. J. et al., *J. Bacteriol.* 169:4177-4183 (1987)), and *streptomyces* bacteriophages such as φC31 (Chater, K. F. et al., In: *Sixth International Symposium on Actinomycetales Biology*, Akademiai Kaido, Budapest, Hungary, pp. 45-54 (1986)). *Pseudomonas* plasmids are reviewed by John, J. F. et al., *Rev. Infect. Dis.* 8:693-704 (1986)), and Izaki, K., *Jon. J. Bacteriol.* 33:729-742 (1978)).

Preferred eukaryotic expression vectors include, without limitation, BPV, vaccinia, 2-micron circle, etc. Such expression vectors are well known in the art (Botstein, D., et al., *Miami Wntr. Symp.* 19:265-274 (1982); Broach, J. R., In: *The Molecular Biology of the Yeast Saccharomyces: Life Cycle and Inheritance*, Cold Spring Harbor Laboratory, Cold Spring Harbor, N.Y. pp. 445-470 (1981); Broach, J. R., *Cell* 28:203-204 (1982); Bollon, D. P., et al., *J. Clin. Hematol. Oncol.* 10:39-48 (1980); Maniatis, T., In: *Cell Biology: A Comprehensive Treatise*, Vol. 3, Gene Expression, Academic Press, NY, pp. 563-608 (1980)).

In addition to microorganisms, cultures of cells derived from multicellular organisms may also be used as hosts. In principle, any such cell culture is workable, whether from vertebrate or invertebrate cellular sources. Interest, however, has been greater with cells from vertebrate sources. Examples of useful vertebrate host cell lines are VERO and HeLa cells, Chinese hamster ovary (CHO) cell lines, WI38, BHK, COS-7, and MDCK cell lines. Expression vectors for such cells ordinarily include (if necessary) an origin of replication, a promoter located in front of or upstream to the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Simian Virus 40 (SV40) and cytomegalovirus. The early and late promoters of SV40 virus are particularly useful because both are obtained easily from the virus as a fragment which also contains the SV40 vial origin of replication (Fiers et al., *Nature* 273:113 (1978)).

An origin of replication may be provided either by construction of the vector to include an exogenous origin, such as may be derived from SV40 or other viral (e.g. Polyoma, Adeno, VSV, BPV) source or may be provided by the host cell chromosomal replication mechanism. If the vector is integrated into the host cell chromosome, the latter is often sufficient.

If cells without formidable cell membrane barriers are used as host cells, transfection is carried out by the calcium phosphate precipitation method as described by Graham and Van der Erb, *Virology* 52:546 (1978). However, other methods for introducing DNA into cells, such as by nuclear injection or by protoplast fusion may also be used. In the case of gene therapy, the direct naked plasmid or viral DNA injection method, with or without transfection-facilitating agents such as, without limitation, liposomes, provides an alternative approach to the current methods of in vivo or in vitro transfection of mammalian cells. If prokaryotic cells or cells which contain substantial cell wall constructions are used, the preferred method of transfection is calcium treatment, using calcium chloride as described in Cohen et al., *Proc. Natl. Acad. Sci. USA* 69:2110 (1972).

IV. Administration and Therapeutic Utility of Compounds of SEQ ID NO:1 or Derivatives Thereof (A) Administration of Compounds of SEQ ID NO:1 or Derivatives Thereof In general, compounds of SEQ ID NO: 1 or derivatives thereof of this invention, or salts thereof, are administered in amounts between about 0.01 and 1 µg/kg body weight per day, preferably from about 0.07 to about 0.2 µg/kg body weight per day. For a 50 kg human female subject, the daily dose of biologically active compounds of SEQ ID NO: 1 or derivatives thereof is from about 0.5 to about 50 µgs, preferably from about 3.5 to about 10 figs. In other mammals, such as horses, dogs, and cattle, higher doses may be required. This dosage may be delivered in a conventional pharmaceutical composition by a single administration, by multiple applications, or via controlled release, as needed to achieve the most effective results, preferably one or more times daily by injection. Most preferably, this dosage may be delivered in a conventional pharmaceutical composition by nasal insufflation.

The selection of the exact dose and composition and the most appropriate delivery regimen will be influenced by, inter alia, the pharmacological properties of the selected compounds of SEQ ID NO: 1 or derivatives thereof, the nature and severity of the condition being treated, and the physical condition and mental acuity of the recipient.

Representative preferred delivery regimens include, without limitation, oral, parenteral (including subcutaneous, transcutaneous, intramuscular and intravenous), rectal, buccal (including sublingual), transdermal, and intranasal insufflation.

Pharmaceutically acceptable salts retain the desired biological activity of the compounds of SEQ ID NO: 1 or derivatives thereof without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like.

A further aspect of the present invention relates to pharmaceutical compositions comprising as an active ingredient compounds of SEQ ID NO: 1 or derivatives thereof of the present invention, or pharmaceutically acceptable salt thereof, in admixture with a pharmaceutically acceptable, non-toxic carrier. As mentioned above, such compositions may be prepared for parenteral (subcutaneous, transcutaneous, intramuscular or intravenous) administration, particularly in the form of liquid solutions or suspensions; for oral or buccal administration, particularly in the form of tablets or capsules; for rectal, transdermal administration; and for intranasal administration, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985), incorporated herein by reference. Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acylcarnitines. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for the most preferred route of administration, nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the polypeptide or its salt dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189, incorporated by reference herein. The compounds or, preferably, their relatively insoluble salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J. R. Robinson ed., Marcel Dekker, Inc., New York, 1978, and R. W. Baker, Controlled Release of Biologically Active Agents, John Wiley & Sons, New York, 1987, incorporated by reference herein.

Like PTH, the compounds of SEQ ID NO:1 and derivatives thereof may be administered in combination with other agents useful in treating a given clinical condition. When treating osteoporosis and other bone-related disorders for example, the compounds of SEQ ID NO:1 and derivatives thereof may be administered in conjunction with a dietary calcium supplement or with a vitamin D analog (see U.S. Pat. No. 4,698,328). Alternatively, the compounds of SEQ ID NO:1 and derivatives thereof may be administered, preferably using a cyclic therapeutic regimen, in combination with bisphosphonates, as described for example in U.S. Pat. No. 4,761,406, or in combination with one or more bone therapeutic agents such as, without limitation, calcitonin and estrogen.

(B) Therapeutic Utility of Compounds of SEQ ID NO: 1 or Derivatives Thereof

Compounds of SEQ ID NO: 1 or derivatives thereof of this invention are useful for the prevention and treatment of a variety of mammalian conditions manifested by loss of bone mass. In particular, the compounds of this invention are indicated for the prophylaxis and therapeutic treatment of osteoporosis and osteopenia in humans. Furthermore, the compounds of this invention are indicated for the prophylaxis and therapeutic treatment of other bone diseases. The compounds of this invention are indicated for the prophylaxis and therapeutic treatment of hypoparathyroidism. Finally, the compounds of this invention are indicated for use as agonists for fracture repair and as antagonists for hypercalcemia.

Some forms of hypercalcemia and hypocalcemia are related to the interaction between PTH and PTHrP and the PTH-1 and PTH-2 receptors. Hypercalcemia is a condition in which there is an abnormal elevation in serum calcium level; it is often associated with other diseases, including hyperparathyroidism, osteoporosis, carcinomas of the breast, lung and prostate, epidermoid cancers of the head and neck and of the esophagus, multiple myeloma, and hypernephroma. Hypocalcemia, a condition in which the serum calcium level is abnormally low, may result from a deficiency of effective PTH, e.g., following thyroid surgery.

Nucleic acids of the invention which encode compounds of SEQ ID NO: 1 or derivatives thereof may also be linked to a selected tissue-specific promoter and/or enhancer and the resultant hybrid gene introduced, by standard methods (e.g., as described by Leder et al., U.S. Pat. No. 4,736,866, herein incorporated by reference), into an animal embryo at an early developmental stage (e.g., the fertilized oocyte stage), to produce a transgenic animal which expresses elevated levels of compounds of SEQ ID NO: 1 or derivatives thereof in selected tissues (e.g., the osteocalcin promoter for bone). Such promoters are used to direct tissue-specific expression of compounds of SEQ ID NO: 1 or derivatives thereof in the transgenic animal.

In addition, any other amino-acid substitutions of a nature, which do not destroy the ability of the PTH analog to antagonize or agonize the PTH-1/PTH-2 receptor (as determined by assays known to the skilled artisan and discussed below), are included in the scope of the present invention.

By "agonist" is intended a ligand capable of enhancing or potentiating a cellular response mediated by the PTH-1/TPH-2 receptor. By "antagonist" is intended a ligand capable of inhibiting a cellular response mediated by the PTH-1/PTH-2 receptor. Whether any candidate "agonist" or "antagonist" of the present invention can enhance or inhibit such a cellular response can be determined using art-known protein ligand/receptor cellular response or binding assays, including those described elsewhere in this application.

In accordance with yet a further aspect of the invention, there is provided a method for treating a medical disorder that results from altered or excessive action of the PTH-1/PTH-2 receptor, comprising administering to a patient a therapeutically effective amount of a compound of SEQ ID NO: 1 or a derivative thereof sufficient to inhibit activation of the PTH-1/PTH-2 receptor of said patient.

In this embodiment, a patient who is suspected of having a disorder resulting from altered action of the PTH-1/PTH-2 receptor may be treated using compounds of SEQ ID NO: 1 or derivatives thereof of the invention which are a selective antagonists of the PTH-1/PTH-2 receptor. Such antagonists include compounds of SEQ ID NO: 1 or derivatives thereof of the invention which have been determined (by the assays described herein) to interfere with PTH-1/PTH-2 receptor-mediated cell activation or other derivatives having similar properties.

To administer the antagonist, the appropriate compound of SEQ ID NO: 1 or a derivative thereof is used in the manufacture of a medicament, generally by being formulated in an appropriate carrier or excipient such as, e.g., physiological saline, and preferably administered intravenously, intramuscularly, subcutaneously, orally, or intranasally, at a dosage that provides adequate inhibition of a compound of SEQ ID NO: 1 or a derivative thereof binding to the PTH-1/PTH-2 receptor. Typical dosage would be 1 ng to 10 mg of the peptide per kg body weight per day.

In a preferred embodiment, the compound of SEQ ID NO: 1 or a derivative thereof used in the method has a single amino acid deletion at the amino terminus. In this preferred embodiment, the PTH analog is [Arg$^{19}$]hPTH(2-28). In yet another preferred embodiment, the compound of SEQ ID NO: 1 or a derivative thereof used in the method has a two amino acid deletion at the amino terminus. In this preferred embodiment, the PTH analog is [Arg$^{19}$]hPTH(3-28).

In accordance with yet a further aspect of the invention, there is provided a method for treating osteoporosis, comprising administering to a patient a therapeutically effective amount of a compound of SEQ ID NO: 1 or a derivative thereof, sufficient to activate the PTH-1/PTH-2 receptor of said patient. Similar dosages and administration as described above for the PTH antagonist, may be used for administration of a PTH agonist, e.g., for treatment of conditions such as osteoporosis, other metabolic bone disorders, and hypoparathyroidism and related disorders.

In a preferred embodiment, the compound of SEQ ID NO: 1 or a derivative thereof used in the method has an amino acid substitution of alanine for serine at amino acid position 1 of compound of SEQ ID NO: 1. In this particular embodiment, the PTH derivative is [Ala$^1$]hPTH(1-28) (SEQ ID NO: 8). In another preferred embodiment, the compound of SEQ ID NO: 1 or a derivative thereof used in the method has an amino acid substitution of arginine for glutamine at position 19 of SEQ ID NO: 1. In this particular embodiment, the PTH derivative is [Arg$^{19}$]hPTH(1-28) (SEQ ID NO: 6). In another preferred embodiment, the compound of SEQ ID NO: 1 or a derivative thereof used in the method has an amino acid substitution of glycine for serine at position 1 of SEQ ID NO: 1. In this particular embodiment, the PTH derivative is [Gly$^1$]hPTH(1-28) (SEQ ID NO: 10). In another preferred embodiment, the compound of SEQ ID NO: 1 or a derivative thereof used in the method has an amino acid substitution of alanine for serine at amino acid position 1 and an amino acid substitution of arginine for glutamine at position 19 of SEQ ID NO: 1. In this particular embodiment, the PTH derivative is [Ala$^1$Arg$^{19}$]hPTH(1-28) (SEQ ID NO: 4). In another preferred embodiment, the compound of SEQ ID NO: 1 or a derivative thereof used in the method has an amino acid substitution of glycine for serine at amino acid position 1 and an amino acid substitution of arginine for glutamine at position 19 of SEQ ID NO: 1. In this particular embodiment, the PTH derivative is [Gly$^1$Arg$^{19}$]hPTH(1-28) (SEQ ID NO: 2).

V. Receptor-Signaling Activities of Compounds of SEQ ID NO: 1 or Derivatives Thereof A crucial step in the expression of hormonal action is the interaction of hormones with receptors on the plasma membrane surface of target cells. The formation of hormone-receptor complexes allows the transduction of extracellular signals into the cell to elicit a variety of biological responses.

A. Screening for PTH-1 Receptor Antagonists and Agonists

Polypeptides of the invention are screened for their agonistic or antagonistic properties using the cAMP accumulation assay. Cells expressing PTH-1 receptor on the cell surface are incubated with native PTH(1-84) for 5-60 minutes at 37° C., in the presence of 2 mM IBMX (3-isobutyl-1-methylxanthine, Sigma, St. Louis, Mo.). Cyclic AMP accumulation is measured by specific radio-immunoassay, as described above. A compound of SEQ ID NO: 1 or a derivative thereof that competes with native PTH(1-84) for binding to the PTH-1 receptor, and that inhibits the effect of native PTH(1-84) on cAMP accumulation, is considered a competitive antagonist. Such a compound would be useful for treating hypercalcemia.

Conversely, a compound of SEQ ID NO: 1 or a derivative thereof that does not compete with native PTH(1-84) for binding to the PTH-1 receptor, but which still prevents native PTH(1-84) activation of cAMP accumulation (presumably by blocking the receptor activation site) is considered a non-competitive antagonist. Such a compound would be useful for treating hypercalcemia.

A compound of SEQ ID NO: 1 or a derivative thereof that competes with native PTH(1-84) for binding to the PTH-1 receptor, and which stimulates cAMP accumulation in the presence or absence of native PTH(1-84) is a competitive agonist. A compound of SEQ ID NO: 1 or a derivative thereof that does not compete with native PTH(1-84) for binding to the PTH-1 receptor but which is still capable of stimulating cAMP accumulation in the presence or absence of native PTH(1-84), or which stimulates a higher cAMP accumulation than that observed by a compound of SEQ ID NO: 1 or a derivative thereof alone, would be considered a non-competitive agonist.

It will be appreciated to those skilled in the art that the invention can be performed within a wide range of equivalent parameters of composition, concentration, modes of administration, and conditions without departing from the spirit or scope of the invention or any embodiment thereof.

Having now fully described the invention, the same will be more readily understood by reference to specific examples which are provided by way of illustration, and are not intended to be limiting of the invention, unless herein specified.

EXAMPLE 1

Materials and Methods

Cell Culture

HKRK B7 or EW5 cells (32), subclones of LLC-PKI renal epithelial cells that stably express human or rat PTH-1 receptors (950,000 and 320,000 receptors/cell, respectively), were maintained under 5% $CO_2$ in air in Dulbecco's modified essential medium containing 7% fetal bovine serum (FBS) and 1% penicillin/streptomycin (GIBCO-BRL, Grand Island, N.Y.). HEK-293 and COS-7 cells were cultured similarly, except that 10% FBS was used in the medium. Cells were seeded into 24-well plates two days before assay at a density of $2-2.5\times10^5$ cells/well (HKRK B7 or EW 5 cells) or $6\times10^5$ cells/well (in 6-well plates) (HEK-293 cells). In experiments involving HEK-293 cells, DNA transfections were performed 24 hr after plating and inositol radiolabel was added 24 hr thereafter (see below). COS-7 cell transfections were performed as previously described (Gardella, T. J., et al., *Endocrinology* 132(5):2024-2030 (1993))

Radioligand Binding and Signaling Assays

Intracellular cAMP accumulation, PLC activation and PTHR binding affinity were measured as previously reported (Bringhurst, F. R., et al., *Endocrinology* 132(5):2090-2098 (1993); Guo, J., et al., *Endocrinology* 136(9):3884-3891 (1995)). Intracellular cAMP accumulation was measured in extracts of cells that were exposed to human PTH peptides in the presence of isobutylmethylxanthine (IBMX, 1 mM) at 37° C. for 15 min. After terminating the reactions by aspiration and freezing in liquid nitrogen, cell monolayers were extracted with 50 mM HCl and cAMP was measured using a radioimmunoassay kit (Dupont-New England Nuclear, Boston, Mass.).

PLC was activated by PTH agonists in the presence of 30 mM LiCl at 37° C. for 30 min after 16 hr of labeling with [$^3$H]myo-inositol (3 uCi/ml) in serum-free medium containing 0.1% bovine serum albumin. The reactions were stopped by rapid aspiration and addition of cold 5% TCA. Water-soluble radiolabeled inositol trisphosphate ($IP_3$) was isolated after ether extraction by ion-exchange chromatography (Guo, J., et al., *Endocrinology* 136(9):3884-3891 (1995)). In experiments involving HEK 293 cells, cells previously transfected with human PTHR cDNA (in the pcDNA1 expression vector HKRK) using Lipofectamine (Gibco BRL) were labeled with [$^3$H]myo-inositol and assayed as described above, except that total water-soluble [$^3$H]inositol polyphosphates were collected as a single fraction from the ion-exchange columns.

Radioligand competition binding assays were performed at 2-8° C. for 6 hr using $^{125}$I-[Nle$^{8,21}$, Tyr$^{34}$]rat PTH-(1-34) (100,000 cpm/well) in the presence or absence of non-radioactive hPTH-(1-34) analogs. Cell layers were washed three times before solubilization for determination of cell-associated radioactivity.

The average levels basally and in the presence of maximal concentrations of hPTH-(1-34) observed in HKRK B7 cells for the assays reported here were 12 ±4 and 207±37 pmoles/well/15 min for cAMP accumulation, 898±142 and 1908 ±251 cpm/well for $IP_3$ formation and 25520±1909 and 956±135 cpm/well for binding, respectively.

Peptides and Other Reagents

All reagents were purchased from Sigma (St. Louis, Mo.), unless otherwise specified. All isotopes were obtained from Dupont-New England Nuclear (Boston, Mass.). Human PTH peptides were synthesized in the Biopolymer Core Laboratory of the Endocrine Unit with C-terminal amidation and, when present, substitution of Tyr$^{34}$ for the naturally occuring Phe$^{34}$. [Tyr$^0$]hPTH-(1-34) was purchased from Sigma Co. $^{125}$I-[Nle$^{8,21}$, Tyr$^{34}$]rat PTH-(1-34) was iodinated and purified as previously described (Bringhurst, F. R., et al., *Endocrinology* 132(5):2090-2098 (1993); Guo, J., et al., *Endocrinology* 136(9):3884-3891 (1995)).

Results

Carboxyl-Truncated PTH Analogs

We previously reported that the C-truncated peptides hPTH-(1-31) and hPTH-(1-30) fully activated both AC and PLC via the human PTH-1 receptor in HKRK B7 cells and that the $EC_{50}$s for these responses were identical, or nearly so, to those seen for hPTH-(1-34) (Takasu, H., and Bringhurst, F. R., *Endocrinology* 139 (10):4293-4299 (1998)). To further define the C-terminal limit for retention of bioactivity, the present analysis of C-truncated hPTH peptides was begun with hPTH-(1-29) and extended to hPTH-(1-24).

As shown in FIG. 1A, hPTH-(1-29) and hPTH-(1-28) activated AC via human PTH-1 receptors in HKRK B7 cells as effectively as did hPTH-(1-34), whereas further shortening (i.e., removal of Leu$^{28}$) strikingly diminished AC activity by approximately 100-fold ($EC_{50}$=100 nM vs. 1 nM). Further truncation, to hPTH-(1-26), produced another 10-fold reduction in potency. The responses to hPTH-(1-26) and hPTH-(1-25) were nearly identical, whereas hPTH-(1-24) was only minimally active at the highest concentration tested (1000 nM).

Profiles of PLC activities of these peptides were strikingly different from those for AC. Thus, PLC activation by hPTH-(1-29) in these cells was dramatically reduced relative to that for hPTH-(1-34) ($EC_{50}$=1000 nM vs. 30 nM). Moreover, hPTH-(1-28) was approximately 5-fold less potent than hPTH-(1-29), and peptides shorter than hPTH-(1-28) failed to significantly increase PLC activity (FIG. 1B). The reductions in PLC activity observed among these C-truncated peptides correlated with measured losses in their binding affinity—i.e., the apparent $IC_{50}$s for binding of hPTH-(1-29) and hPTH-(1-28) also were reduced 30-100 fold, compared with that of hPTH-(1-34), and no displacement of radioligand occurred with peptides shorter than hPTH-(1-28) at concentrations as high as 1000 nM (FIG. 1C).

Figure 3:
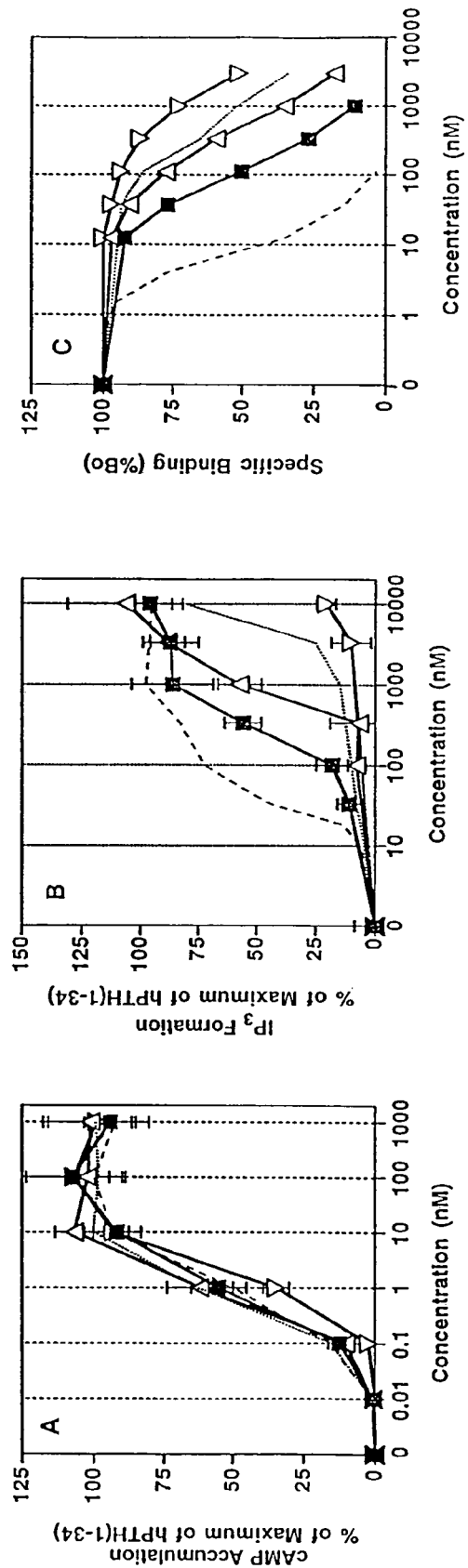
FIG. 3. Effects of mutations at positions 1 or 19 on properties of hPTH-(1-28) in HKRK B7 cells. Intracellular cAMP accumulation (A), $IP_3$ formation (B) and competitive radioligand binding (C) are depicted for $[Arg^{19}]$hPTH-(1-28) (■) (SEQ ID NO: 6), $[Ala^1]$hPTH-(1-28) (Δ) (SEQ ID NO: 8), and $[Gly^1]$hPTH-(1-28) (∇) (SEQ ID NO: 10) added at the concentrations indicated. Results are expressed as described in FIG. 1. For reference, responses for hPTH-(1-34) (SEQ ID NO: 14) and hPTH-(1-28) (SEQ ID NO: 12) previously shown in FIG. 1 are replotted using dashed and dotted lines, respectively.

To determine if the progressive loss of PLC activity associated with stepwise C-terminal truncation of PTH-(1-34) was due to the observed parallel loss in binding affinity or, instead, to coincidental deletion of a critical PLC activation domain, we introduced into hPTH-(1-28) a modification—substitution of Arg for Glu at position 19—that previously was reported to enhance binding of hPTH-(1-34) to rodent PTH receptors (Gardella, T. J., et al., *J. Biol. Chem.* 270(12): 6584-6588 (1995)). The resulting peptide, [Arg$^{19}$]hPTH-(1-28), exhibited both enhanced binding (IC$_{50}$=100 nM vs. 1000 nM) and increased PLC activity (EC$_{50}$=300 nM vs. 6000 nm), relative to hPTH-(1-28) (see FIG. 3). Importantly, this [Arg$^{19}$]hPTH-(1-28) analog maximally activated PLC, despite absence of the hPTH-(29-32) sequence reported to be essential for PKC activation (Jouishomme, H., et al., *J. Bone Miner. Res.* 9(6):943-949 (1994); Jouishomme, H., et al., *Endocrinology* 130(1):53-60 (1992)). Adenylyl cyclase activity was unaffected by the Arg$^{19}$ substitution (FIG. 3A). As these results suggested that amino acids C-terminal to position 28 of hPTH, while important for optimal ligand binding, are not required for maximal PLC activation via the human PTH receptor, we then focused upon the role of the N-terminus of hPTH in PLC activation.

N-Terminally Modified hPTH Analogs

Human PTH-(3-34) had been characterized previously as a PLC/PKC-selective peptide via rodent PTH receptors (Azarani, A., et al., *J. Biol. Chem.* 271(25):14931-14936 (1996); Fujimori, A., et al., *Endocrinology* 128(6):3032-3039 (1991); Jouishomme, H., et al., *Endocrinology* 130(1):53-60 (1992)). We have observed, however, that this peptide, at concentrations as high as 1000 nM, did not activate PLC in HKRK B7 cells or in COS-7 cells that expressed rat or human PTH-1 receptors (Takasu et al., *J. Bone Miner. Res.*, In Press). These results indicated that the first two amino acids at the N-terminus of hPTH-(1-34) (Ser$^1$-Val$^2$) must be important for PLC as well as AC activation via the human PTH receptor.

To refine this analysis, we first studied the properties of hPTH-(2-34). As shown in FIGS. 2A & 2B, hPTH-(2-34) did not elicit PLC activity in HKRK B7 cells, even though its activation of AC was comparable in magnitude and sensitivity to that of hPTH-(1-34). Similar results were obtained using COS-7 cells expressing abundant human PTH-1 receptors (data not shown). The inability of hPTH-(2-34) to activate PLC via human PTH-1 receptors was confirmed in a fully homologous system by using HEK-293 human embryonic kidney cells that were transiently transfected with human PTH-1 receptor cDNA (Table 1).

TABLE 1

Activation of PLC by hPTH Peptides in Transiently Transfected HEK-293 Cells

| Human PTH Peptide | PLC Activity (% Basal) |
| --- | --- |
| Control | 100 ± 11 |
| hPTH-(1-34) | 854 ± 188* |
| hPTH-(1-28) | 305 ± 20* |
| hPTH-(1-27) | 95 ± 23 |
| hPTH-(2-34) | 88 ± 23 |
| desamino[Ala$^1$]hPTH-(1-34) | 106 ± 20 |
| desamino[Gly$^1$]hPTH-(1-34) | 108 ± 12 |

Total inositol polyphosphate produced in response to 1000 nM of the peptides shown were measured in HEK-293 cells that transiently expressed human PTH-1 receptors. Results are expressed as means±SEMs of the % of basal activity for triplicate determinations. The basal level of total IPs in controls was 578±91 cpm/well/30 min. * Significantly different from controls (p<0.05)

We next addressed the role of the N-terminal Ser$^1$ residue and of its α-amino group in binding to and activation of the human PTH-1 receptor. Because earlier work with isolated rat renal membranes had shown that substitution of Ala$^1$ for Ser$^1$ in hPTH-(1-34) increased its AC activity, whereas a Gly$^1$ substitution impaired AC activation by bPTH-(1-34) (Tregear, G. W., and Potts, J. T., Jr. *Endocr. Res. Commun.* 2:561-567 (1975)), these position-1 modifications were introduced into hPTH-(1-34), with the results shown in FIG. 2. The [Ala$^1$]hPTH-(1-34) analog was indistinguishable from hPTH-(1-34) with respect to binding as well as activation of AC or PLC, whereas the Gly$^1$-substituted peptide showed diminished PLC activity (25% of the hPTH-(1-34) maximum) at the highest concentration tested (1000 nM) despite unchanged binding affinity and AC activity).

Figure 2:
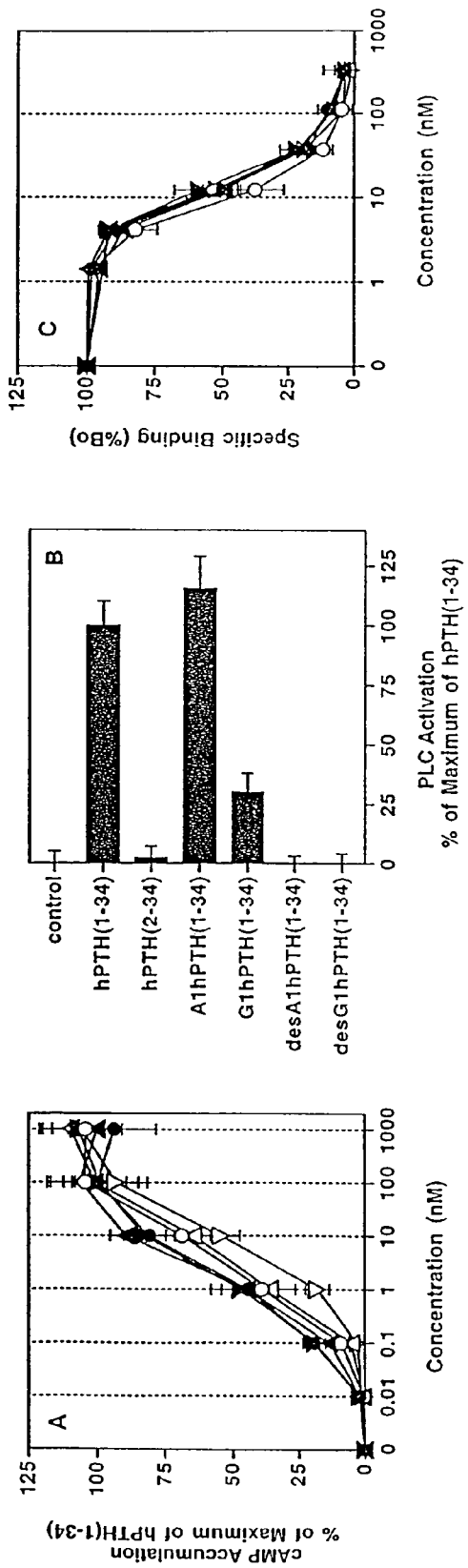
FIG. 2. Properties of N-terminally modified hPTH-(1-34) analogs in HKRK B7 cells. (A) Intracellular cAMP accumulation in response to the indicated concentrations of: hPTH-(1-34) (●) (SEQ ID NO: 14), hPTH-(2-34) (○) (SEQ ID NO: 15), $[Ala^1]$hPTH-(1-34) (▲) (SEQ ID NO: 20), $[Gly^1]$hPTH-(1-34) (▼) (SEQ ID NO: 21), desamino-$[Ala^1]$hPTH-(1-34) (Δ) (SEQ ID NO: 22), and desamino-$[Gly^1]$hPTH-(1-34) (∇) (SEQ ID NO: 24); (B) Formation of $IP_3$ in response to 1000 nM of the indicated peptides; (C) Competitive radioligand binding of the same peptides denoted in panel A. Results are expressed as described in FIG. 1.

Deletion of the α-amino groups of these Ala$^1$- and Gly$^1$-substituted hPTH-(1-34) (i.e., desamino[Ala$^1$]hPTH-(1-34) and desamino[Gly$^1$]hPTH-(1-34), respectively) resulted in complete loss of detectable PLC activity in HKRK B7 cells, although there was no change in apparent binding affinity and no more than a 2 to 5-fold reduction in AC potency (FIG. 2). These results were confirmed using COS-7 cells expressing rat or human PTH-1 receptors (not shown) and in studies of HEK-293 human kidney cells transiently transfected with human PTH-1 receptor cDNA (Table 1). Removal of the α-amino group of hPTHrP(1-36) also eliminated PLC activation by that ligand in HKRK B7 cells [i.e., hPTHrP(1-36) =178±12; desamino-hPTHrP(1-36)=101±6 percent of basal, respectively, at 1000 nM peptide]. Displacement of the N-terminal α-amino group by interposition of a tyrosine residue at the N-terminus of hPTH-(1-34) (i.e. [Tyr$^0$]hPTH-(1-34)) also abolished PLC activity (105±5 percent of basal at 1000 nM peptide). Collectively, these findings pointed to a critical role for the N-terminal residue of hPTH-(1-34), and of its free α-amino group in particular, in the activation of PLC by the human PTH-1 receptor. As the impact of each position-1 change was both relatively selective for PLC (vs. AC) in these cells and independent of changes in binding affinity, a strategy was suggested for potentially dissociating PLC from AC activation via the PTH-1 receptor.

Modifications of hPTH-(1-28)

As shown earlier (FIG. 1), hPTH-(1-28) was the shortest analog of hPTH-(1-34) that, at the highest concentration tested (10 μM), still could activate both AC and PLC via the human PTH-1 receptor in HKRK B7 cells. When Ala$^1$ was substituted for Ser$^1$ in the hPTH-(1-28) sequence, binding affinity and the EC$_{50}$ for PLC activation both were partially improved, although not to the extent observed previously with [Arg$^{19}$]hPTH-(1-28) (FIGS. 3B and 3C). Activation of AC, already equivalent to that of hPTH-(1-34), was not further enhanced. In contrast, the Gly$^1$ substitution (i.e. [Gly$^1$] hPTH-(1-28)) selectively eliminated PLC signaling, apart from a weak response at 10 μM, and modestly impaired binding affinity (FIGS. 3B and 3C).

Figure 4:
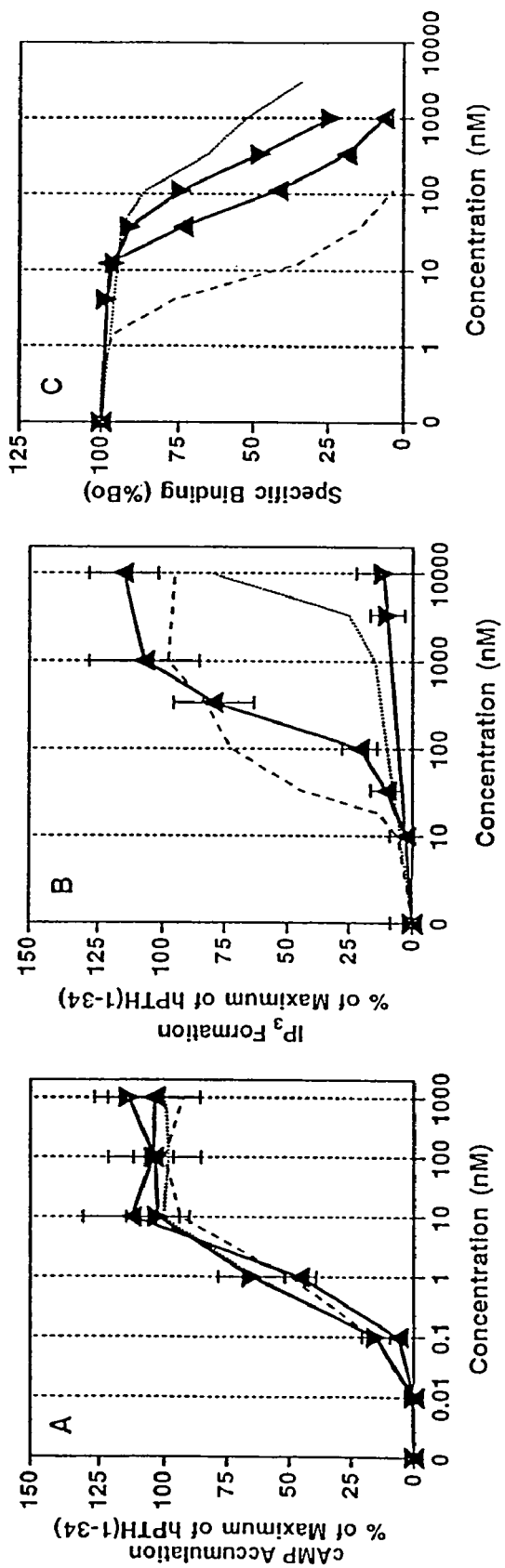
FIG. 4. Effects of mutations at positions 1 and 19 on properties of hPTH-(1-28) in HKRK B7 cells. Intracellular cAMP accumulation (A), $IP_3$ formation (B) and competitive radioligand binding (C) are depicted for $[Ala^1, Arg^{19}]$hPTH-(1-28) (▲) (SEQ ID NO: 4) and $[Gly^1, Arg^{19}]$hPTH-(1-28) (▼) (SEQ ID NO: 2) at the indicated concentrations. Results are expressed as described in FIG. 1. For reference, responses for hPTH-(1-34) (SEQ ID NO: 14) and hPTH-(1-28) (SEQ ID NO: 12) are shown as in FIG. 3.

When the binding-enhancing Arg$^{19}$ modification was superimposed upon the [Ala$^1$]hPTH-(1-28) and [Gly$^1$]hPTH-(1-28) analogs, binding affinity of these peptides for the human PTHR was increased by 5-10 fold (FIG. 4C—compare with FIG. 3C). In the case of [Ala$^1$,Arg$^{19}$]hPTH-(1-28), the EC$_{50}$ for PLC activation also was improved 5-fold [i.e., from. 1000 nM (FIG. 3B) to 200 nM (FIG. 4B)] over that of [Ala$^1$]hPTH-(1-28). Interestingly, the Ala$^1$,Arg$^{19}$ double substitution could not restore PLC activity to hPTH-(1-27), however, although it did improve the $EC_{50}$ for AC activation by 10-fold (Table 2, FIG. 1).

TABLE 2

Activities of [Ala1, Arg19]hPTH-(1-27) in HKRK B7 cells.

| Concentration (nM) | Cyclic AMP accumulation (% Maximum) | | IP$_3$ Formation (% Maximum) | |
|---|---|---|---|---|
| | hPTH-(1-34) | [Ala$^1$, Arg$^{19}$]hPTH-(1-27) | hPTH-(1-34) | [Ala$^1$, Arg$^{19}$]hPTH-(1-27) |
| 0.01 | 1.7 ± 0.7 | −0.2 ± 0.1 | | |
| 0.1 | 14 ± 1.4 | 0.6 ± 0.3 | | |
| 1 | 45 ± 7.8 | 7 ± 0.6 | | |
| 10 | 93 ± 8.1 | 50 ± 5.1 | | |
| 100 | 96 ± 9.5 | 92 ± 15 | | |
| 1000 | 100 ± 12 | 99 ± 8.8 | 87 ± 2.8 | 1.5 ± 4.8 |
| 10000 | | | 100 ± 13 | 6.9 ± 10 |

Signaling responses were measured as described in Methods in cells stimulated by hPTH-(1-34) or [Ala$^1$,Arg$^{19}$]hPTH-(1-27). Results were expressed as a % of the maximal response to hPTH-(1-34) observed in the same assay. Values are the mean±SEM of 4 (cAMP accumulation) and 6 (IP$_3$ formation) measurements obtained in two separate experiments performed in duplicate and triplicate, respectively.

In contrast to [Ala$^1$,Arg$^{19}$]hPTH-(1-28), there was no increase in PLC activity following introduction of the Arg$^{19}$ substitution into [Gly$^1$]hPTH-(1-28) despite a comparable 5-fold improvement in binding affinity (FIG. 4), Thus, the AC activation curves for both [Ala$^1$,Arg$^{19}$]hPTH-(1-28) and [Gly$^1$,Arg$^{19}$]hPTH-(1-28) were indistinguishable from that of hPTH-(1-34) (FIG. 4A), whereas the PLC response profiles demonstrated that [Gly$^1$,Arg$^{19}$]hPTH-(1-28), unlike [Ala$^1$,Arg$^{19}$] hPTH-(1-28), was strikingly and selectively impaired with respect to activation of this signaling pathway.

The possibility that the [Gly$^1$,Arg$^{19}$]hPTH-(1-28) peptide might be useful, especially in rodent models, as a signal-selective analog to dissociate AC from PLC signaling via the PTH-1 receptor was examined further using the EW5 subclone of LLC-PK1 cells that stably expresses rat PTH-1 receptors (Guo, J., et al., *Endocrinology* 136(9):3884-3891 (1995)). As shown in Table 3, the signaling and binding properties of the various substituted hPTH-(1-28) analogs in EW5 cells were similar, though not identical, to those described above in HKRK B7 cells. Differences noted for the hPTH-(1-28) peptides between the rat and human receptors included: (1) signaling of hPTH-(1-28) via the rat PTH-1 receptors was more severely impaired than via the human PTH-1 receptor, despite comparable binding affinity (compare Table 3 and FIG. 1); (2) the Gly$^1$ substitution slightly enhanced (by 2-fold) binding affinity of hPTH-(1-28) peptides for the rat PTH-1 receptor, whereas it impaired binding to the human PTH-1 receptor by about 3-fold (compare Table 3 with FIGS. 3 and 4); and (3) the binding affinity and $EC_{50}$ for AC of [Gly$^1$,Arg$^{19}$]hPTH-(1-28) for the rat PTH-1 receptor were impaired only about 6-fold, relative to hPTH-(1-34), whereas binding of this analog to the human PTH-1 receptor was reduced almost 40-fold. Although the efficacy of [Gly$^1$, Arg$^{19}$]hPTH(1-28) for activation of AC via the human PTH-1 receptor was similar to that of hPTH-(1-34) in HKRK-B7 cells, it was reduced up to 10-20 fold, concordant with its reduced binding affinity, in other cells (LLC-PKI or SaOS-2 osteosarcoma) that expressed many fewer human PTH-1 receptors (i.e. 10,000-100,000 vs. 950,000 per cell) (data not shown). Overall, the results indicated that the [Gly$^1$,Arg$^{19}$] hPTH-(1-28) peptide is highly signal selective for AC vs. PLC via the both the rat and human PTH-1 receptors and that it may be especially useful, due to its well-preserved binding affinity, for studies with rodent models in vivo.

Discussion

Several major conclusions regarding the interaction of hPTH-(1-34) and the PTH-1 receptor can be drawn from the results of these experiments. First, it is clear that an intact N-terminus of the hPTH-(1-34) ligand is indispensible for effective activation of PLC via the PTH-1 receptor. The C-terminus of hPTH-(1-34), especially the sequence hPTH-(28-30), contributes to effective PLC activation by stabilizing ligand binding but is not required for maximal PLC activation if binding can be maintained by other means. Second, although the N-terminus of hPTH is important for activation of both AC and PLC via the PTH-1 receptor, the roles of specific structural features within the N-terminus of the ligand in activating these two effectors are different. Specifically, we found that PLC activation is much more sensitive to the structure of the N-terminus—i.e. both the identity of the N-terminal amino acid and the presence of the N-terminal α-amino group—than is the AC response, which, unlike PLC, can occur normally even in the absence of an amino acid at position 1. Thirdly, because of this difference in sensitivity of AC and PLC signaling to changes at the N-terminus of the hPTH peptide, it is possible, as shown here for the [Gly$^1$, Arg$^{19}$]hPTH-(1-28) analog, to dissociate activation of these two effectors by altering the structure of the ligand. We had previously accomplished such signaling selectivity through mutations in the PTH-1 receptor (by changing the EKKY sequence in intracellular loop 2 to DSEL (Iida-Klein, A., et al., *J. Biol. Chem.* 272(11):6882-6889 (1997)), but it now is clear that a highly signal-selective ligand, active through the wild type receptor, also can be designed.

These findings require that some key concepts regarding the structural determinants of PTH signaling be re-examined. Work conducted previously with rodent and opossum cells that express endogenous PTH-1 receptors had shown that N-truncated PTH analogs, such as PTH-(3-34), lack AC activity but nevertheless can potently activate PKC and, in some systems (Donahue, H. J., et al., *J. Biol. Chem.* 263: 13522-13527 (1988); Fujimori, A., et al., *Endocrinology* 128 (6):3032-3039 (1991); Siegfried, G., et al., *Endocrinology* 136(3): 1267-1275 (1995)), but not others (Reid, I. R., et al., *Am. J. Physiol.* 253(1 Pt 1):E45-51 (1987); Tamura, T., et al., *Biochem. Biophys.,Res. Commun.* 159:1352-1358 (1989)), $Ca_i^{++}$ transients. Detailed analysis of the PKC-activating properties of N- and C-truncated hPTH-(1-34) analogs led to the conclusion that the sequence hPTH-(29-32) represents a critical "PKC activation domain" (Jouishomme, H., et al., *J. Bone Miner. Res.* 9(6):943-949 (1994); Jouishomme, H., et al., *Endocrinology* 130(1):53-60 (1992); Whitfield, J. F., and Morley, P. *Trends Pharm. Sci.* 16(11):382-386 (1995)).

The vigorous PLC activation that we observed with C-truncated analogs such as [Ala$^1$,Arg$^{19}$]hPTH-(1-28) clearly indicates that the hPTH-(29-32) region is not required for full activation of PLC via the human PTH-1 receptor. Our results do show that this region is important for high-affinity binding of the hPTH-(1-34) ligand to its receptor, as reported previously for bPFH-(1-34) in rat renal membranes (Segre, G. V., et al., *J. Biol. Chem.* 254:6980-6986 (1979)). At the same time, it is apparent that the PLC response of the human PTH-1 receptor is more sensitive than is the AC response to reductions in ligand-binding affinity. This conclusion also is consistent with the fact that PLC is more strongly dependent upon the level of PTH-1 receptor surface expression (Guo, J., et al., *Endocrinology* 136(9):3884-3891 (1995)).

Previous studies of the effects of hPTH-(1-34) or PTH-(3-34) on PLC activation or $Ca_i^{++}$ signaling via recombinant human PTH-1 receptors expressed heterologously in COS-7 or HEK-293 cells produced discordant findings (Pines, M., et al., *Bone* 18(4):381-389 (1996); Seuwen, K., et al., *Brit. J. Pharm.* 114(8):1613-1620 (1995); Jobert, A.-S., et al., *Endocrinology* 138(12):5282-5292 (1997); Schneider, H., et al., *FEBS Lett.* 351(2):281-285 (1994)). Because of the numerous observations that N-terminally truncated PTH analogs trigger activation of PKC and $Ca_i^{++}$ in other systems (Azarani, A., et al., *J. Biol. Chem.* 271(25):14931-14936 (1996); Donahue, H. J., et al., *J. Biol. Chem.* 263:13522-13527 (1988); Fujimori, A., et al., *Endocrinology* 128(6):3032-3039 (1991); Fujimori, A., et al., *Endocrinology* 130(1):29-36 (1992); Janulis, M., et al., *Endocrinology* 133:713-719 (1993); Jouishomme, H., et al., *Endocrinology* 130(1):53-60 (1992); Chakravarthy, B. R., et al., *Biochem. Biophys. Res. Commun.* 171(3):1105-1110 (1990); Cole, J. A., et al., *Endocrinology* 1229:2981-2989 (1988); Rixon, R. H., et al., *J. Bone Miner. Res.* 9(8):1179-1189 (1994)), however, our finding that a free α-amino group at position-I of hPTH-(1-34) is an absolute requirement for PLC activation via the human PTH-1 receptor was quite unexpected. In fact, our data indicate that PLC activation via the PTH-1 receptor is even more sensitive to such subtle N-terminal modifications than is AC, and, in contrast to the consequences of stepwise C-terminal truncation of hPTH-(1-34), the reduction in PLC potency of these analogs cannot be attributed to lower binding affinity. This suggests that the extreme N-terminus of hPTH-(1-34) constitutes a true "activation domain" for PLC signaling via the human PTH-1 receptor. We should note that others previously have reported activation of PLC by the N-truncated peptides bPTH-(2-34) and bPTH-(3-34) in rat UMR 106-01 osteosarcoma cells (Fujimori, A., et al., *Endocrinology* 128 (6):3032-3039 (1991)). The explanation for this discrepancy could lie in species differences (in cells and ligand) or in the possible expression by UMR osteosarcoma cells of alternate species of PLC-coupled PTH-1 receptors, the presence of which could not be excluded in rat osteosarcoma cells that also expressed endogenous PTH-1 receptors (Murray, T. M., et al., *Calcif. Tiss. Internat.* 49(2):120-123 (1991); Inomata, N., et al., *Endocrinology* 136(11):4732-4740 (1995)). The failure of N-truncated hPTH-(1-34) analogs studied here to activate PLC via cloned human PTH-1 receptors was not unique to the porcine host cells, however, as these findings were confirmed in both COS-7 cells and in a homologous human cell system as well.

Our results are not inconsistent with observations that the C-terminal portion of hPTH-(1-34) activates PKC via the PTH-1 receptor (Azarani, A., et al., *J. Biol. Chem.* 271(25):14931-14936 (1996); Janulis, M., et al., *Endocrinology* 133:713-719 (1993); Jouishomme, H., et al., *J. Bone Miner. Res.* 9(6):943-949 (1994); Siegfried, G., et al., *Endocrinology* 136 (3):1267-1275 (1995); Jouishomme, H., et al., *Endocrinology* 130(1):53-60 (1992)). Protein kinase C may be activated by mechanisms other than PLC, including phospholipase D and phospholipase $A_2$ ($PLA_2$) (Nishizuka, Y., *FASEB J.* 9:484-496 (1995)). Indeed, in renal cells PTH may activate PLA2 (42) and may stimulate PKC without increasing PLC (Friedman, P. A., et al., *Endocrinology* 137(1):13-20 (1996)). Similarly, evidence has been provided for PLC-independent mechanisms of PTH-stimulated $Ca_i^{++}$ transients via the human PTH-1 receptor (Seuwen, K., et al., *Brit. J. Pharm.* 114(8):1613-1620 (1995); Jobert, A.-S., et al., *Endocrinology* 138(12):5282-5292 (1997)), which could explain activation of $Ca_i^{++}$ by N-truncated PTH analogs that we have shown not to stimulate PLC (Donahue, H. J. et al., *J. Biol. Chem.* 263: 13522-13527 (1988); Fujimori, A., et al., *Endocrinology* 128 (6):3032-9 (1991); Jouishomme, H., et al., *Endocrinology* 130(1):53-60(1992)). Thus, it may be that the C-terminal domain of PTH-(1-34) is involved in activating such alternate pathways of PKC or $Ca_1^{++}$ activation. If so, our results lead to the conclusion that at least three activation domains reside within the hPTH-(1-34) molecule—two at the N-terminus that mediate activation of AC and PLC and one near the C-terminus that activates PKC via one or more PLC-independent mechanisms. Further clarification of the significance of these various activation domains for physiological or pharmacological actions of PTH in vivo will require better definition of the roles of key cellular pathways activated by PTH-1 receptor-mediated AC, PLC and PKC signaling. These issues now can be addressed more clearly by comparing biological actions of the C-truncated/N-terminally modified PTH analogs described here with those of N-terminally shortened PTH analogs described by others (Azarani, A., et al., *J. Biol. Chem.* 271(25):14931-14936 (1996); Janulis, M., et al., *Endocrinology* 133:713-719 (1993); Siegfried, G., et al., *Endocrinology* 136(3):1267-1275 (1995); Rixon, R. H., et al., *J. Bone Miner. Res.* 9(8):1179-1189 (1994)) that trigger PKC activation but not PLC. For example, we previously found that selective ablation of the PLC response to PTH-(1-34) via mutations within the second intracellular loop of the rat PTH-1 receptor blocks certain downstream biologic responses, such as sodium-dependent phosphate transport in LLC-PK1 cells (Iida-Klein, A., et al., *J. Biol. Chem.* 272(11): 6882-6889 (1997)) and interleukin-6 production by growth-plate chondrocytes (unpublished data). The availability of novel ligands with selective signaling via the wild type PTH-1 receptor now offers a complementary approach to addressing such questions in vitro. Ultimately, careful correlation of in vitro tests with studies of analog activity in vivo will be required to dissect and fully define the physiological roles of these separate PTH-1 receptor signals.

Amino-truncated analogs, including bPTH-(2-34), hPTH-(2-38) and desamino-PTH-(1-34), previously were found to exhibit only weak AC activity when tested in vitro (Fujimori, A., et al., *Endocrinology* 128(6):3032-3039 (1991); Fujimori, A., et al., *Endocrinology* 130(1):29-36 (1992); Tregear, G. W., and Potts, J. T., Jr. *Endocr. Res. Commun.* 2:561-567 (1975); Rixon, R. H., et al., *J. Bone Miner. Res.* 9(8):1179-1189 (1994)), whereas we found that hPTH-(2-34), desamino-[Ala$^1$]hPTH-(1-34) and desamino-[Gly$^1$]hPTH-(1-34) were equipotent with hPTH-(1-34). This disparity likely is explained by the much larger number of human PTH-1 receptors expressed by the HKRK B7 cells than by the osteosarcoma cells or partially purified membranes used in previous studies (Fujimori, A., et al., *Endocrinology* 128(6):3032-3039 (1991); Fujimori, A., et al., *Endocrinology* 130(1):29-36 (1992); Tregear, G. W., and Potts, J. T., Jr. *Endocr. Res. Commun.* 2:561-567 (1975); Rixon, R. H., et al., *J. Bone Miner. Res.* 9(8):1179-1189 (1994)). The HKRK B7 cells were selected for our studies to optimize analysis of the structural basis of PLC signaling via human PTH-1 receptors, which requires a high level of receptor expression (Guo, J., et al., *Endocrinology* 136(9):3884-3891 (1995); Pines, M., et al., *Endocrinology* 135(4):1713-1716 (1994)). When these N-truncated peptides were tested with other LLC-PK1 subclones that expressed fewer human PTH-1 receptors (i.e. 100,000-300,000 per cell), their AC responses were indeed reduced by as much as 10-fold, relative to hPTH-(1-34) (data not shown). On the other hand, studies of such N-truncated PTH analogs in vivo have demonstrated greater biopotency than predicted from measures of AC activity in vitro (Tregear, G. W., et al., *Endocrinology* 93:1349-1353 (1973); Hilliker, S., et al., *Bone* 19:469-477 (1996)). Also, the actual number of PTH-1 receptors expressed by relevant target cells in vivo remains uncertain but could be within the range studied here (Shukunarni, C., et al., *J. Cell Biol.* 133(2):457-468 (1996); Bos, M. P., et al., *Calcif. Tiss. Internat.* 58(2):95-100 (1996)).

This is the first demonstration that peptides shorter than PTH-(1-28) can fully activate AC via the PTH-1 receptor. In previous studies using isolated renal membranes or ROS 17/2 osteosarcoma cells, little or no activity was detected with PTH-(1-27) or shorter C-truncated analogs (Segre, G. V., et al., *J. Biol. Chem.* 254:6980-6986 (1979); Tregear, G. W., et al., *Endocrinology* 93:1349-1353 (1973); Neugebauer, W., et al., *Biochemistry* 34(27):8835-8842 (1995)). Moreover, scanning mutagenesis had identified a critical role in binding to the rat PTH-1 receptor for Leu2, which is believed to be important in stabilizing an α-helix near the C-terminus of the hPTH-(1-34) molecule (Gombert, F., et al., in *Proc. 14th Am. Peptide Symp.*, Kaumaya, P. and Hodges, R., eds., Mayflower Scientific Limited, Kingswinford, UK (1996), pp. 661-662; Neugebauer, W., et al., *Biochemistry* 34(27):8835-8842 (1995)). As described above for the N-truncated peptides, our ability to detect AC activation by C-truncated hPTH peptides shorter than hPTH-(1-28) likely is due to the high level of human PTH-1 receptor expression in the cells we used. Transiently transfected COS-7 or HEK 293 cells, which have been widely used in structure-function studies of both PTH and the PTH-1 receptor, typically express at least as many receptors as do HKRK B7 cells (lida-Klein, A., et al., *J. Biol. Chem.* 270(15):8458-8465 (1995)). Of course, until physiologic levels of PTH-1 receptor expression have been defined in relevant target cells in vivo, estimates of the AC activity of PTH analogs or mimetic compounds obtained using these highly sensitive in vitro systems must be interpreted cautiously. At the same time, such systems appear to offer important advantages for identifying weak human PTH-1 receptor agonists and defining the elemental structural features of ligands involved in binding and multiple parallel signaling by this receptor.

Finally, our studies of modified hPTH-(1-28) analogs have identified a novel hPTH analog, [$Gly^1,Arg^{19}$]hPTH-(1-28), that exhibits marked (>40-fold) selectivity, relative to hPTH-(1-34), for activation of AC (vs. PLC) via the human PTH-1 receptor. In HKRK B7 cells that express abundant human PTH-1 receptor, activation of AC by this analog was equivalent to that by hPTH(1-34), despite a 30-fold lower binding affinity, whereas PLC potency was reduced approximately 100-fold. Although, like hPTH-(2-34) and the desamino analogs, the absolute AC potency of [$Gly^1,Arg^{19}$]hPTH-(1-28) is reduced in cells that express many fewer human PTH-1 receptors/cell, this peptide nevertheless retains sufficient binding affinity and AC activity to prove useful as a signal-selective PTHR-agonist for studies of the signaling basis of specific PTH actions in target cells that express human PTH-1 receptors. The [$Gly^1,Arg^{19}$]hPTH-(1-28) analog should be particularly useful for both in vitro and in vivo studies in rodent systems. This peptide is >10-fold selective for AC vs. PLC via the rat PTH-1 receptor. Moreover, its binding affinity for the rat PTH-1 receptor is 10-fold greater than for the human PTH-1 receptor and only 7-fold less than that of hPTH-(1-34). Careful analysis of the properties of this analog in vitro and in vivo should help clarify the role of PTH-1 receptor-dependent PLC activation in PTH action(s) and provide further direction for the development of other signal-selective hPTH analogs.

What is claimed is:

1. A method for treating a mammalian subject having a condition characterized by a decrease in bone mass, said method comprising administering to said subject an effective bone mass-increasing amount of a biologically active peptide consisting essentially of the formula:
   (a) $X_{01}$ValSerGluIleGlnLeuMetHisAsnLeuGlyLysHisLeuAsnSerMet$X_{02}$ArgValGluTrpLeuArgLysLysLeu (SEQ ID NO:1);
   (b) fragments thereof containing amino acids 1-24, 1-25, 1-26, or 1-27;
   (c) pharmaceutically acceptable salts thereof; or
   (d) N- or C-terminal chemical derivatives thereof;
   wherein:
   $X_{01}$ is Ser, Ala or Gly; and
   $X_{02}$ is Glu or Arg,
   provided that said peptide is not hPTH(1-26)NH$_2$, hPTH(1-27)NH$_2$ or hPTH(1-28)NH$_2$; and a pharmaceutically acceptable carrier.

2. The method of claim 1, wherein the condition to be treated is osteoporosis.

3. The method of claim 2, wherein said osteoporosis is old age osteoporosis.

4. The method of claim 2, wherein said osteoporosis is post-menopausal osteoporosis.

5. The method of claim 1, wherein the effective amount of said peptide for increasing bone mass is from about 0.01 μg/kg/day to about 1.0 μg/kg/day.

6. The method of claim 1, wherein the method of administration is parenteral.

7. The method of claim 1, wherein the method of administration is subcutaneous.

8. The method of claim 1, wherein the method of administration is nasal insufflation.

9. The method of claim 1, wherein the method further comprises the administration of a compound selected from the group consisting of: a dietary calcium supplement, a vitamin D analog, a bisphosphonate, calcitonin and estrogen.

10. The method of claim 1, wherein the condition to be treated is selected from the group consisting of: hypoparathyroidism, fracture repair and osteopenia.

11. The method of claim 1, wherein said peptide is Gly-ValSerGluIleGlnLeuMetHisAsn-LeuGlyLysHisLeuAsnSerMetArgArgValGluTrpLeu ArgLysLysLeu (SEQ ID NO:2).

12. The method of claim 1, wherein said peptide is Ala-ValSerGluIleGlnLeuMetHisAsn-LeuGlyLysHisLeuAsnSerMetArgArgValGluTrpLeu ArgLysLysLeu (SEQ ID NO:4).

13. The method of claim 1, wherein said peptide is SerValSerGluIleGlnLeuMetHisAsnLeuG-lyLysHisLeuAsnSerMetArgArgValGluTrpLeu ArgLysLysLeu (SEQ ID NO:6).

14. The method of claim 1, wherein said peptide is Ala-ValSerGluIleGlnLeuMetHisAsn-LeuGlyLysHisLeuAsnSerMetGluArgValGluTrpLeu ArgLysLysLeu (SEQ ID NO:8).

15. The method of claim 1, wherein said peptide is Gly-ValSerGluIleGlnLeuMetHisAsn-LeuGlyLysHisLeuAsnSerMetGluArgValGluTrpLeu ArgLysLysLeu (SEQ ID NO:10).

* * * * *

UNITED STATES PATENT AND TRADEMARK OFFICE
CERTIFICATE OF CORRECTION

PATENT NO. : 7,479,478 B2
APPLICATION NO. : 10/959605
DATED : January 20, 2009
INVENTOR(S) : F. Richard Bringhurst et al.

It is certified that error appears in the above-identified patent and that said Letters Patent is hereby corrected as shown below:

On the Title Page, Item (56), under References Cited, under OTHER PUBLICATIONS, under "Takasu, H., and Bringhurst, P.R.", replace "Bringhurst, P.R." with --Bringhurst, F.R.--;

Column 1, Line 59, replace "Sarnra" with --Samra--;

Column 3, Line 18, replace "(1994);)" with --(1994))--;

Column 4,
    Line 16, replace "$X_{01}$ ValSerGluIleGluGln" with --$X_{01}$ValSerGluIleGln--;
    Line 33, replace "$X_{01}$ ValSerGluIleGlnLeuMetHisAsnLeuGlyLysAsnSerMet" with --$X_{01}$ ValSerGluIleGlnLeuMetHisAsnLeuGlyLysHisLeuAsnSerMet--;

Column 5,
    Line 49, replace "receptor of said patient" with --receptor of said patient.--;
    Line 57, replace "flourescent" with --fluorescent--;

Column 7,
    Line 40, replace "organsim" with --organism--;
    Line 42, replace "polydeoxribonucleotide" with --polydeoxyribonucleotide--;

Column 12, Line 59, replace "GIn" with --Gln--;

Column 13,
    Line 7, replace "GlIn" with --Gln--;
    Line 24, replace "of present invention" with --of the present invention--;

Signed and Sealed this

Twenty-fourth Day of August, 2010

David J. Kappos
*Director of the United States Patent and Trademark Office*

Column 15,
    Line 5, replace "recA. lacZ. lacI." with --recA, lacZ, lacI,--;
    Line 9, replace "Bacillius" with --Bacillus--;
    Line 31, replace "may employed" with --may be employed--;

Column 19,
    Line 25, replace "TPH-2 receptor" with --PTH-2 receptor--;
    Line 42, replace "which are a selective" with --which are selective--;

Column 22, Line 25, replace "occuring" with --occurring--.

SEQUENCE LISTING

```
<160> NUMBER OF SEQ ID NOS: 13

<210> SEQ ID NO 1
<211> LENGTH: 28
<212> TYPE: PRT
<213> ORGANISM: Homo sapiens
<220> FEATURE:
<221> NAME/KEY: UNSURE
<222> LOCATION: (1)..(1)
<223> OTHER INFORMATION: Can be Ser, Ala or Gly
<220> FEATURE:
<221> NAME/KEY: UNSURE
<222> LOCATION: (19)..(19)
<223> OTHER INFORMATION: Can be Glu or Arg

<400> SEQUENCE: 1

Xaa Val Ser Glu Ile Gln Leu Met His Asn Leu Gly Lys His Leu Asn
1               5                   10                  15

Ser Met Xaa Arg Val Glu Trp Leu Arg Lys Lys Leu
            20                  25

<210> SEQ ID NO 2
<211> LENGTH: 28
<212> TYPE: PRT
<213> ORGANISM: Homo sapiens

<400> SEQUENCE: 2

Gly Val Ser Glu Ile Gln Leu Met His Asn Leu Gly Lys His Leu Asn
1               5                   10                  15
```

```
Ser Met Arg Arg Val Glu Trp Leu Arg Lys Lys Leu
            20                  25
```

```
<210> SEQ ID NO 3
<211> LENGTH: 27
<212> TYPE: PRT
<213> ORGANISM: Homo sapiens

<400> SEQUENCE: 3

Gly Val Ser Glu Ile Gln Leu Met His Asn Leu Gly Lys His Leu Asn
1               5                   10                  15

Ser Met Arg Arg Val Glu Trp Leu Arg Lys Lys
            20                  25
```

```
<210> SEQ ID NO 4
<211> LENGTH: 28
<212> TYPE: PRT
<213> ORGANISM: Homo sapiens

<400> SEQUENCE: 4

Ala Val Ser Glu Ile Gln Leu Met His Asn Leu Gly Lys His Leu Asn
1               5                   10                  15

Ser Met Arg Arg Val Glu Trp Leu Arg Lys Lys Leu
            20                  25
```

```
<210> SEQ ID NO 5
<211> LENGTH: 27
<212> TYPE: PRT
<213> ORGANISM: Homo sapiens

<400> SEQUENCE: 5

Ala Val Ser Glu Ile Gln Leu Met His Asn Leu Gly Lys His Leu Asn
1               5                   10                  15

Ser Met Arg Arg Val Glu Trp Leu Arg Lys Lys
            20                  25
```

```
<210> SEQ ID NO 6
<211> LENGTH: 28
<212> TYPE: PRT
<213> ORGANISM: Homo sapiens

<400> SEQUENCE: 6

Ser Val Ser Glu Ile Gln Leu Met His Asn Leu Gly Lys His Leu Asn
1               5                   10                  15

Ser Met Arg Arg Val Glu Trp Leu Arg Lys Lys Leu
            20                  25
```

```
<210> SEQ ID NO 7
<211> LENGTH: 27
<212> TYPE: PRT
<213> ORGANISM: Homo sapiens

<400> SEQUENCE: 7

Ser Val Ser Glu Ile Gln Leu Met His Asn Leu Gly Lys His Leu Asn
1               5                   10                  15

Ser Met Arg Arg Val Glu Trp Leu Arg Lys Lys
            20                  25
```

```
<210> SEQ ID NO 8
<211> LENGTH: 28
<212> TYPE: PRT
<213> ORGANISM: Homo sapiens
```

<400> SEQUENCE: 8

Ala Val Ser Glu Ile Gln Leu Met His Asn Leu Gly Lys His Leu Asn
1               5                   10                  15

Ser Met Glu Arg Val Glu Trp Leu Arg Lys Lys Leu
            20                  25

<210> SEQ ID NO 9
<211> LENGTH: 27
<212> TYPE: PRT
<213> ORGANISM: Homo sapiens

<400> SEQUENCE: 9

Ala Val Ser Glu Ile Gln Leu Met His Asn Leu Gly Lys His Leu Asn
1               5                   10                  15

Ser Met Glu Arg Val Glu Trp Leu Arg Lys Lys
            20                  25

<210> SEQ ID NO 10
<211> LENGTH: 28
<212> TYPE: PRT
<213> ORGANISM: Homo sapiens

<400> SEQUENCE: 10

Gly Val Ser Glu Ile Gln Leu Met His Asn Leu Gly Lys His Leu Asn
1               5                   10                  15

Ser Met Glu Arg Val Glu Trp Leu Arg Lys Lys Leu
            20                  25

<210> SEQ ID NO 11
<211> LENGTH: 27
<212> TYPE: PRT
<213> ORGANISM: Homo sapiens

<400> SEQUENCE: 11

Gly Val Ser Glu Ile Gln Leu Met His Asn Leu Gly Lys His Leu Asn
1               5                   10                  15

Ser Met Glu Arg Val Glu Trp Leu Arg Lys Lys
            20                  25

<210> SEQ ID NO 12
<211> LENGTH: 28
<212> TYPE: PRT
<213> ORGANISM: Homo sapiens

<400> SEQUENCE: 12

Ser Val Ser Glu Ile Gln Leu Met His Asn Leu Gly Lys His Leu Asn
1               5                   10                  15

Ser Met Glu Arg Val Glu Trp Leu Arg Lys Lys Leu
            20                  25

<210> SEQ ID NO 13
<211> LENGTH: 27
<212> TYPE: PRT
<213> ORGANISM: Homo sapiens

<400> SEQUENCE: 13

Ser Val Ser Glu Ile Gln Leu Met His Asn Leu Gly Lys His Leu Asn
1               5                   10                  15

Ser Met Glu Arg Val Glu Trp Leu Arg Lys Lys
            20                  25